US011351264B2

(12) United States Patent
Boitano et al.

(10) Patent No.: US 11,351,264 B2
(45) Date of Patent: Jun. 7, 2022

(54) PAR2 MIMETIC PEPTIDES AND USES THEREOF

(71) Applicants: ARIZONA BOARD OF REGENTS ON BEHALF OF THE UNIVERSITY OF ARIZONA, Tucson, AZ (US); BOARD OF REGENTS, THE UNIVERSITY OF TEXAS SYSTEM, Austin, TX (US)

(72) Inventors: Scott A. Boitano, Tucson, AZ (US); Josef Vagner, Tucson, AZ (US); Theodore J. Price, Austin, TX (US)

(73) Assignees: ARIZONA BOARD OF REGENTS ON BEHALF OF THE UNIVERSITY OF ARIZONA, Tucson, AZ (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 466 days.

(21) Appl. No.: 16/090,525

(22) PCT Filed: Mar. 31, 2017

(86) PCT No.: PCT/US2017/025511
§ 371 (c)(1),
(2) Date: Oct. 1, 2018

(87) PCT Pub. No.: WO2017/173347
PCT Pub. Date: Oct. 5, 2017

(65) Prior Publication Data
US 2019/0117785 A1 Apr. 25, 2019

Related U.S. Application Data

(60) Provisional application No. 62/317,305, filed on Apr. 1, 2016.

(51) Int. Cl.
| | |
|---|---|
| A61K 38/08 | (2019.01) |
| C07K 7/00 | (2006.01) |
| A61K 47/60 | (2017.01) |
| C07K 14/705 | (2006.01) |
| C07K 5/083 | (2006.01) |
| C07K 5/10 | (2006.01) |
| A61K 47/61 | (2017.01) |
| C07K 5/103 | (2006.01) |
| C07K 1/22 | (2006.01) |
| C12N 9/76 | (2006.01) |
| C12N 9/64 | (2006.01) |
| C07K 5/117 | (2006.01) |
| C07K 5/062 | (2006.01) |
| A61K 47/62 | (2017.01) |
| A61K 47/54 | (2017.01) |
| A61K 38/17 | (2006.01) |
| A61K 38/00 | (2006.01) |

(52) U.S. Cl.
CPC ............ *A61K 47/60* (2017.08); *A61K 38/177* (2013.01); *A61K 47/542* (2017.08); *A61K 47/543* (2017.08); *A61K 47/545* (2017.08); *A61K 47/61* (2017.08); *A61K 47/62* (2017.08); *C07K 1/22* (2013.01); *C07K 5/06034* (2013.01); *C07K 5/081* (2013.01); *C07K 5/0808* (2013.01); *C07K 5/10* (2013.01); *C07K 5/101* (2013.01); *C07K 5/1013* (2013.01); *C07K 5/1024* (2013.01); *C07K 14/705* (2013.01); *C12N 9/6427* (2013.01); *C12N 9/6445* (2013.01); *A61K 38/00* (2013.01)

(58) Field of Classification Search
None
See application file for complete search history.

(56) References Cited

U.S. PATENT DOCUMENTS

2006/0104944 A1    5/2006   Mousa

FOREIGN PATENT DOCUMENTS

WO    WO 03/009940    2/2003

OTHER PUBLICATIONS

Drumm et al, Genetic Variation and Clinical Heterogeneity in Cystic Fibrosis, Annu. Rev. Pathol. Mech. Dis., 2012, 7, pp. 267-282 (Year: 2012).*
Yampolsky et al, The Exchangeability of Amino Acids in Proteins, Genetics, 2005, 170, pp. 1459-1472. (Year: 2005).*
Heuberger et al, Protease-activated receptors (PARs): mechanisms of action and potential therapeutic modulators in PAR-driven inflammatory diseases, Thrombosis Journal, 2019, 17, pp. 1-24 (Year: 2019).*
Abassi, Y. A., et al., Kinetic cell-based morphological screening: prediction of mechanism of compound action and off-target effects. Chem Biol. Jul. 31, 2009;16(7):712-23.
Adams, M.N., et al., Structure, function and pathophysiology of protease activated receptors. Pharmacol Ther. Jun. 2011;130(3):248-82.

(Continued)

*Primary Examiner* — Julie Ha
*Assistant Examiner* — Kristina M Hellman
(74) *Attorney, Agent, or Firm* — Casimir Jones, S.C.; Robert A. Goetz

(57) ABSTRACT

This invention is in the field of medicinal pharmacology. In particular, the invention relates to protease activated receptor type 2 (PAR2) modulating compounds (e.g., mimetic peptides), compositions comprising such modulating compounds, and their use as therapeutics for the treatment of conditions involving PAR2 activity.

6 Claims, 12 Drawing Sheets
Specification includes a Sequence Listing.

(56) References Cited

OTHER PUBLICATIONS

Asiedu, M.N. et al., Spinal protein kinase M ζ0 underlies the maintenance mechanism of persistent nociceptive sensitization. J Neurosci. May 4, 2011;31(18):6646-53.
Bao, Y, et al., Protease-activated receptor 2 signalling pathways: a role in pain processing. Expert Opin Ther Targets. Jan. 2014;18(1):15-27.
Bao, Y., et al., PAR2-mediated upregulation of BDNF contributes to central sensitization in bone cancer pain. Mol Pain. May 5, 2014;10:28.
Barry, G. D., et al., Novel agonists and antagonists for human protease activated receptor 2. J Med Chem. Oct. 28, 2010;53(20):7428-40.
Bauer, R. A., et al., Expanding the range of 'druggable' targets with natural product-based libraries: an academic perspective. Curr Opin Chem Biol. Jun. 2010;14(3):308-14.
Berg, K. A., et al., Effector pathway-dependent relative efficacy at serotonin type 2A and 2C receptors: evidence for agonist-directed trafficking of receptor stimulus. Mol Pharmacol. Jul. 1998;54(1):94-104.
Bernstein, C. et al., Sensitization of the trigeminovascular pathway: perspective and implications to migraine pathophysiology. J Clin Neurol. Jun. 2012;8(2):89-99.
Blackhart, B. D., et al., Ligand cross-reactivity within the protease-activated receptor family. J Biol Chem. Jul. 12, 1996;271(28):16466-71.
Boitano, S, et al. Development and evaluation of small peptidomimetic ligands to protease-activated receptor-2 (PAR2) through the use of lipid tethering. PLoS One. Jun. 13, 2014;9(6):e99140.
Boitano, S, et al., The novel PAR2 ligand C391 blocks multiple PAR2 signalling pathways in vitro and in vivo. Br J Pharmacol. Sep. 2015;172(18):4535-4545.
Boitano, S. et al., Potent agonists of the protease activated receptor 2 (PAR2). J Med Chem. Mar. 10, 2011;54(5):1308-13.
Boitano, S., et al., Alternaria alternata serine proteases induce lung inflammation and airway epithelial cell activation via PAR2. Am J Physiol Lung Cell Mol Physiol. Apr. 2011;300(4):L605-14.
Bunnett, NW. Protease-activated receptors: how proteases signal to cells to cause inflammation and pain. Semin Thromb Hemost. Apr. 2006;32 Suppl 1:39-48.
Cattaruzza, F. et al., Cathepsin S is activated during colitis and causes visceral hyperalgesia by a PAR2-dependent mechanism in mice. Gastroenterology. Nov. 2011;141(5):1864-74.e1-3.
Cenac, N. et al., Role for protease activity in visceral pain in irritable bowel syndrome. J Clin Invest. Mar. 2007;117(3):636-47.
Chen, H., Kovar, et al., A cell-based immunocytochemical assay for monitoring kinase signaling pathways and drug efficacy. Anal Biochem. Mar. 1, 2005;338(1):136-42.
Cowell, S. M., et al., Intelligent design in combinatorial chemistry: use of designed peptide libraries to explore secondary and tertiary structures in peptides and proteins. Methods Enzymol. 2003;369:288-97.
Dai, Y, et al., Proteinase-activated receptor 2-mediated potentiation of transient receptor potential vanilloid subfamily 1 activity reveals a mechanism for proteinase-induced inflammatory pain. J Neurosci. May 5, 2004;24(18):4293-9.
Day, S. B., et al., German cockroach frass proteases modulate the innate immune response via activation of protease-activated receptor-2. J Innate Immun. 2010;2(5):495-504.
Defea, K. A. Stop that cell! Beta-arrestin-dependent chemotaxis: a tale of localized actin assembly and receptor desensitization. Annu Rev Physiol. 2007;69:535-60.
Defea, K. A., et al., beta-arrestin-dependent endocytosis of proteinase-activated receptor 2 is required for intracellular targeting of activated ERK1/2. J Cell Biol. Mar. 20, 2000;148(6):1267-81.
Defea, K. Beta-arrestins and heterotrimeric G-proteins: collaborators and competitors in signal transduction. Br J Pharmacol. Mar. 2008;153 Suppl 1:S298-309.

Flynn, A.N. et al., Development of highly potent protease-activated receptor 2 agonists via synthetic lipid tethering. FASEB J. Apr. 2013;27(4):1498-510.
Flynn, A.N. et al., The protease-activated receptor-2-specific agonists 2-aminothiazol-4-yl-LIGRL-NH2 and 6-aminonicotinyl-LIGRL-NH2 stimulate multiple signaling pathways to induce physiological responses in vitro and in vivo. J Biol Chem. May 27, 2011;286(21):19076-88.
Frye, S., et al., US academic drug discovery. Nat Rev Drug Discov. Jun. 2011;10(6):409-10.
Gardell, L. R., et al., Identification and characterization of novel small-molecule protease-activated receptor 2 agonists. J Pharmacol Exp Ther. Dec. 2008;327(3):799-808.
Ge, L., et al., A beta-arrestin-dependent scaffold is associated with prolonged MAPK activation in pseudopodia during protease-activated receptor-2-induced chemotaxis. J Biol Chem. Sep. 5, 2003;278(36):34418-26.
Goede, A., et al., SuperMimic-fitting peptide mimetics into protein structures. BMC Bioinformatics. Jan. 10, 2006;7:11.
Goh, F.G., et al., Dual effect of the novel peptide antagonist K-14585 on proteinase-activated receptor-2-mediated signalling. Br J Pharmacol. Dec. 2009;158(7):1695-704.
Gough, S. C. Liraglutide: from clinical trials to clinical practice. Diabetes Obes Metab. Apr. 2012;14 Suppl 2:33-40.
Grant, A.D., et al., Protease-activated receptor 2 sensitizes the transient receptor potential vanilloid 4 ion channel to cause mechanical hyperalgesia in mice. J Physiol. Feb. 1, 2007;578(Pt 3):715-33.
Hansen, KK, et al., Proteinases as hormones: targets and mechanisms for proteolytic signaling. Biol Chem. Aug. 2008;389(8):971-82.
Hoffman, J., et al., Lanthanide labeling of a potent protease activated receptor-2 agonist for time-resolved fluorescence analysis. Bioconjug Chem. Oct. 17, 2012;23(10):2098-104.
Hollenberg, M. D., et al., Derivatized 2-furoyl-LIGRLO-amide, a versatile and selective probe for proteinase-activated receptor 2: binding and visualization. J Pharmacol Exp Ther. Aug. 2008;326(2):453-62.
Hollenberg, M. D., et al., Kallikreins and proteinase-mediated signaling: proteinase-activated receptors (PARs) and the pathophysiology of inflammatory diseases and cancer. Biol Chem. Jun. 2008;389(6):643-51.
Hollenberg, M.D., et al., Biased signalling and proteinase-activated receptors (PARs): targeting inflammatory disease. Br J Pharmacol. Mar. 2014;171(5):1180-94.
Hruby, V. J. (2002) Designing peptide receptor agonists and antagonists. Nat Rev Drug Discov 1, 847-858.
Hruby, V. J., et al., Conformational and topographical considerations in designing agonist peptidomimetics from peptide leads. Curr Med Chem. Sep. 2000;7(9):945-70.
Hruby, V. J., et al., Design of nonpeptides from peptide ligands for peptide receptors. Methods Enzymol. 2002;343:91-123.
International Search Report and Written Opinion, International Patent Application No. PCT/US2017/025511, dated Aug. 25, 2017, 12 pages.
Ishihara, H., et al., Protease-activated receptor 3 is a second thrombin receptor in humans. Nature. Apr. 3, 1997;386(6624):502-6.
Jacquet, A. Interactions of airway epithelium with protease allergens in the allergic response. Clin Exp Allergy. Mar. 2011;41(3):305-11.
Jalink, K., et al., G protein-coupled receptors: the inside story. Bioessays. Jan. 2010;32(1):13-6.
Josan, J. S., et al., Solid-phase synthetic strategy and bioevaluation of a labeled delta-opioid receptor ligand Dmt-Tic-Lys for in vivo imaging. Org Lett. Jun. 18, 2009;11(12):2479-82.
Kawabata, A. et al., Suppression of pancreatitis-related allodynia/hyperalgesia by proteinase-activated receptor-2 in mice. Br J Pharmacol. May 2006;148(1):54-60.
Kawabata, A., et al., Evaluation of proteinase-activated receptor-1 (PAR1) agonists and antagonists using a cultured cell receptor desensitization assay: activation of PAR2 by PAR1-targeted ligands. J Pharmacol Exp Ther. Jan. 1999;288(1):358-70.

(56) References Cited

OTHER PUBLICATIONS

Kawabata, Potent and metabolically stable agonists for protease-activated receptor-2: evaluation of activity in multiple assay systems in vitro and in vivo. J Pharmacol Exp Ther. Jun. 2004;309(3):1098-107.

Lam, D.K., et al., Novel animal models of acute and chronic cancer pain: a pivotal role for PAR2. J Neurosci. Oct. 10, 2012;32(41):14178-83.

Lam, D.K., et al., Serine proteases and protease-activated receptor2-dependent allodynia: a novel cancer pain pathway. Pain. May 2010;149(2):263-72.

Lee, H. J., et al., Protease-activated receptor 2 mediates mucus secretion in the airway submucosal gland. PLoS One. 2012;7(8):e43188.

Lee, Y. S., et al., Opioid and melanocortin receptors: do they have overlapping pharmacophores? Biopolymers. 2008;90(3):433-8.

Levy, D., Migraine pain and nociceptor activation—where do we stand? Headache. May 2010;50(5):909-16.

Lindner, J. R., et al., Delayed onset of inflammation in protease-activated receptor-2-deficient mice. J Immunol. Dec. 1, 2000;165(11):6504-10.

Liu, Q., et al., The distinct roles of two GPCRs, MrgprC11 and PAR2, in itch and hyperalgesia. Sci Signal. Jul. 12, 2011;4(181):ra45.

Liu, S. et al., Protease-activated receptor 2 in dorsal root ganglion contributes to peripheral sensitization of bone cancer pain. Eur J Pain. Mar. 2014;18(3):326-37.

Lohse, M. J. (2010) Dimerization in GPCR mobility and signaling. Curr Opin Pharmacol. Feb. 2010;10(1):53-8.

Madsen, K., et al., Structure-activity and protraction relationship of long-acting glucagon-like peptide-1 derivatives: importance of fatty acid length, polarity, and bulkiness. J Med Chem. Nov. 29, 2007;50(24):6126-32.

Maryanoff, B. E., et al., Protease-activated receptor-2 (PAR-2): structure-function study of receptor activation by diverse peptides related to tethered-ligand epitopes. Arch Biochem Biophys. Feb. 15, 2001;386(2):195-204.

Mayorov, A. V., et al., Structure-activity relationships of cyclic lactam analogues of alpha-melanocyte-stimulating hormone (alpha-MSH) targeting the human melanocortin-3 receptor. J Med Chem. Jan. 24, 2008;51(2):187-95. Epub Dec. 19, 2007.

McGuire, J. J., et al., 2-furoyl-LIGRLO-amide: a potent and selective proteinase-activated receptor 2 agonist. J Pharmacol Exp Ther. Jun. 2004;309(3):1124-31.

Melemedjian, O.K. et al., IL-6- and NGF-induced rapid control of protein synthesis and nociceptive plasticity via convergent signaling to the elF4F complex. J Neurosci. Nov. 10, 2010;30(45):15113-23.

Melemedjian, O.K., et al., BDNF regulates atypical PKC at spinal synapses to initiate and maintain a centralized chronic pain state. Mol Pain. Mar. 20, 2013;9:12.

Melemedjian, O.K., et al., Local translation and retrograde axonal transport of CREB regulates IL-6-induced nociceptive plasticity. Mol Pain. Jul. 4, 2014;10:45.

Millar, R. P., et al., The year in G protein-coupled receptor research. Mol Endocrinol. Jan. 2010;24(1):261-74.

Nichols, H. L., et al., beta-Arrestin-2 mediates the proinflammatory effects of protease-activated receptor-2 in the airway. Proc Natl Acad Sci U S A. Oct. 9, 2012;109(41):16660-5.

Nystedt, S., et al., Molecular cloning and functional expression of the gene encoding the human proteinase-activated receptor 2. Eur J Biochem. Aug. 15, 1995;232(1):84-9.

Oikonomopoulou, K., et al., Proteinase-activated receptors, targets for kallikrein signaling. J Biol Chem. Oct. 27, 2006;281(43):32095-112.

Ossovskaya, V.S. et al., Protease-activated receptors: contribution to physiology and disease. Physiol Rev. Apr. 2004;84(2):579-621.

Page, K., et al., Mucosal sensitization to German cockroach involves protease-activated receptor-2. Respir Res. May 24, 2010;11:62.

Pal, K., et al., Divergent beta-arrestin-dependent signaling events are dependent upon sequences within G-protein-coupled receptor C termini. J Biol Chem. Feb. 1, 2013;288(5):3265-74.

Peters, T. et al., Protease-activated receptors and prostaglandins in inflammatory lung disease. Br J Pharmacol. Oct. 2009;158(4):1017-33.

Rajagopal, S., et al., Teaching old receptors new tricks: biasing seven-transmembrane receptors. Nat Rev Drug Discov. May 2010;9(5):373-86.

Ramachandran, R. et al., Proteinases and signalling: pathophysiological and therapeutic implications via PARs and more. Br J Pharmacol. Mar. 2008;153 Suppl 1:S263-82.

Ramachandran, R. et al., Targeting proteinase-activated receptors: therapeutic potential and challenges. Nat Rev Drug Discov. Jan. 3, 2012;11(1):69-86.

Ramachandran, R., et al., Agonist-biased signaling via proteinase activated receptor-2: differential activation of calcium and mitogen-activated protein kinase pathways. Mol Pharmacol. Oct. 2009;76(4):791-801.

Ramachandran, R., et al., Neutrophil elastase acts as a biased agonist for proteinase activated receptor-2 (PAR2). J Biol Chem. Jul. 15, 2011;286(28):24638-48.

Reed, CE, et al., The role of protease activation of inflammation in allergic respiratory diseases. J Allergy Clin Immunol. Nov. 2004;114(5):997-1008; quiz 1009.

Reichling, D.B., et al., Critical role of nociceptor plasticity in chronic pain. Trends Neurosci. Dec. 2009;32(12):611-8.

Roman, K., et al., Tryptase-PAR2 axis in experimental autoimmune prostatitis, a model for chronic pelvic pain syndrome. Pain. Jul. 2014;155(7):1328-38.

Rothmeier, A. S., et al., Protease-activated receptor 2 signaling in inflammation. Semin Immunopathol. Jan. 2012;34(1):133-49.

Scarborough, R. M. Protease-activated receptor-2 antagonists and agonists. Curr Med Chem Cardiovasc Hematol Agents. Mar. 2003;1(1):73-82.

Schreiber, S. L. Organic synthesis toward small-molecule probes and drugs. Proc Natl Acad Sci U S A. Apr. 26, 2011;108(17):6699-702.

Sherwood, C. L., et al., Arsenic alters ATP-dependent $Ca^{2+}$ signaling in human airway epithelial cell wound response. Toxicol Sci. May 2011;121(1):191-206.

Sherwood, C. L., et al., Chronic arsenic exposure in nanomolar concentrations compromises wound response and intercellular signaling in airway epithelial cells. Toxicol Sci. Mar. 2013;132(1):222-34.

Snelgrove, RJ, et al., Alternaria-derived serine protease activity drives IL-33-mediated asthma exacerbations. J Allergy Clin Immunol. Sep. 2014;134(3):583-592.e6.

Soh, U. J., et al., Signal transduction by protease-activated receptors. Br J Pharmacol. May 2010;160(2):191-203.

Søreide, K. Proteinase-activated receptor 2 (PAR-2) in gastrointestinal and pancreatic pathophysiology, inflammation and neoplasia. Scand J Gastroenterol. Aug. 2008;43(8):902-9.

Stallaert, W., et al., Impedance responses reveal beta(2)-adrenergic receptor signaling pluridimensionality and allow classification of ligands with distinct signaling profiles. PLoS One. 2012;7(1):e29420.

Stevens, A. J., et al., The role of public-sector research in the discovery of drugs and vaccines.N Engl J Med. Feb. 10, 2011;364(6):535-41.

Suen, JY, et al., Modulating human proteinase activated receptor 2 with a novel antagonist (GB88) and agonist (GB110). Br J Pharmacol. Mar. 2012;165(5):1413-23.

Suen, J.Y., et al., Pathway-selective antagonism of proteinase activated receptor 2. Br J Pharmacol. Sep. 2014;171(17):4112-24.

Takizawa, T., et al., Abrogation of bronchial eosinophilic inflammation and attenuated eotaxin content in protease-activated receptor 2-deficient mice. J Pharmacol Sci. May 2005;98(1):99-102.

Tillu, DV, et al. Protease-activated receptor 2 activation is sufficient to induce the transition to a chronic pain state. Pain. May 2015;156(5):859-67.

Vagner, J., et al., Peptidomimetics, a synthetic tool of drug discovery. Curr Opin Chem Biol. Jun. 2008;12(3):292-6.

Vergnolle, N. Protease-activated receptors as drug targets in inflammation and pain. Pharmacol Ther. Sep. 2009;123(3):292-309.

(56) References Cited

OTHER PUBLICATIONS

Vergnolle, N., et al., Proteinase-activated receptor 2 (PAR2)-activating peptides: identification of a receptor distinct from PAR2 that regulates intestinal transport. Proc Natl Acad Sci U S A. Jun. 23, 1998;95(13):7766-71.

Vergnolle, N., et al., Proteinase-activated receptor-2 and hyperalgesia: A novel pain pathway. Nat Med. Jul. 2001;7(7):821-6.

Vos, T., et al., Years lived with disability (YLDs) for 1160 sequelae of 289 diseases and injuries 1990-2010: a systematic analysis for the Global Burden of Disease Study 2010. Lancet. Dec. 15, 2012;380(9859):2163-96.

Vu, T. K., et al., Molecular cloning of a functional thrombin receptor reveals a novel proteolytic mechanism of receptor activation. Cell. Mar. 22, 1991;64(6):1057-68.

Weiner, M.L. Intestinal transport of some macromolecules in food. Food Chem Toxicol. Oct. 1988;26(10):867-80.

Wong, S. K. A 384-well cell-based phospho-ERK assay for dopamine D2 and D3 receptors. Anal Biochem. Oct. 15, 2004;333(2):265-72.

Xi, B., et al., The application of cell-based label-free technology in drug discovery. Biotechnol J. Apr. 2008;3(4):484-95.

Xu, W. F., et al., Cloning and characterization of human protease-activated receptor 4. Proc Natl Acad Sci U S A. Jun. 9, 1998;95(12):6642-6.

Yamamoto, T., et al., A structure-activity relationship study and combinatorial synthetic approach of C-terminal modified bifunctional peptides that are delta/mu opioid receptor agonists and neurokinin 1 receptor antagonists. J Med Chem. Mar. 13, 2008;51(5):1369-76.

Yamamoto, T., et al., The biological activity and metabolic stability of peptidic bifunctional compounds that are opioid receptor agonists and neurokinin-1 receptor antagonists with a cystine moiety. Bioorg Med Chem. Oct. 15, 2009;17(20):7337-43.

Yau, MK, et al., Toward drugs for protease-activated receptor 2 (PAR2). J Med Chem. Oct. 10, 2013;56(19):7477-97.

Ying, J., et al., Design, synthesis, and biological evaluation of new cyclic melanotropin peptide analogues selective for the human melanocortin-4 receptor. J Med Chem. Nov. 16, 2006;49(23):6888-96.

Zhang, W. et al., Proteinase-activated receptor 2 mediates thermal hyperalgesia and is upregulated in a rat model of chronic pancreatitis. Pancreas. Mar. 2011;40(2):300-7.

Zhang, X.C. et al., Modulation of meningeal nociceptors mechanosensitivity by peripheral proteinase-activated receptor-2: the role of mast cells. Cephalalgia. Mar. 2008;28(3):276-84.

Zheng, H., et al., Agonist-selective signaling of G protein-coupled receptor: mechanisms and implications. IUBMB Life. Feb. 2010;62(2):112-9.

Zoudilova, M., et al., Beta-arrestin-dependent regulation of the cofilin pathway downstream of protease-activated receptor-2. J Biol Chem. Jul. 13, 2007;282(28):20634-46.

Zoudilova, M., et al., beta-Arrestins scaffold cofilin with chronophin to direct localized actin filament severing and membrane protrusions downstream of protease-activated receptor-2. J Biol Chem. May 7, 2010;285(19):14318-29.

\* cited by examiner

FIG. 2A

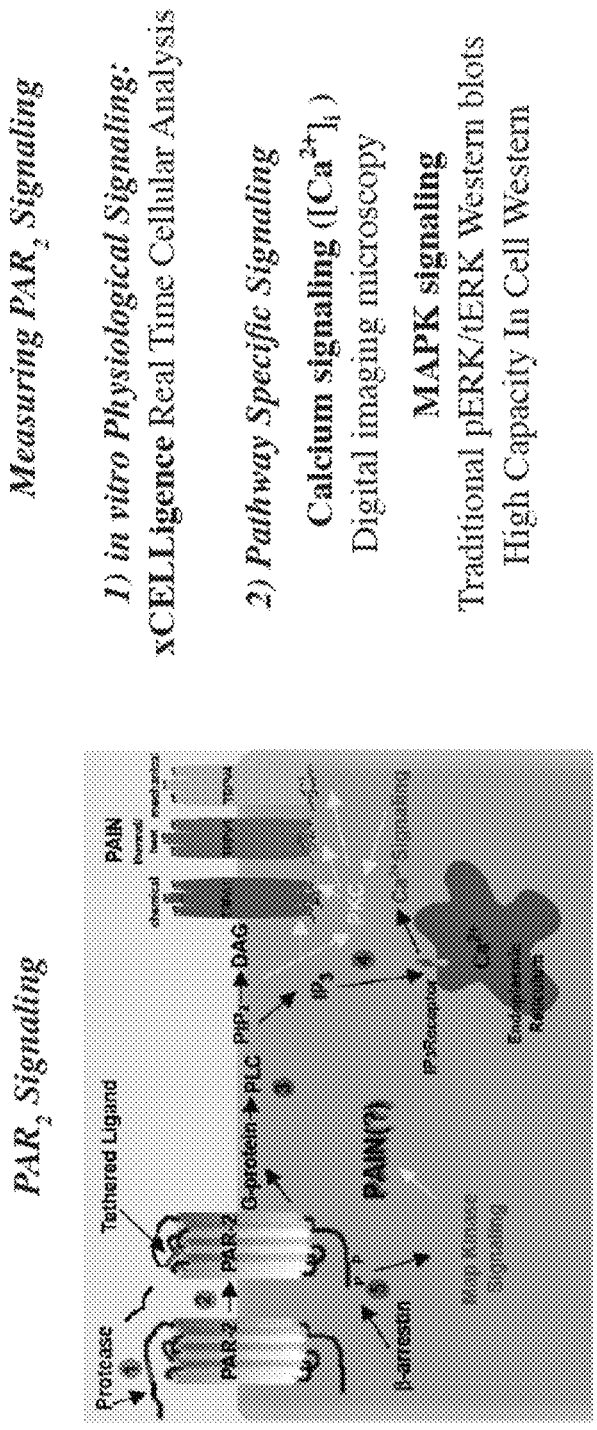

*Measuring PAR₂ Signaling*

1) *in vitro Physiological Signaling:*
xCELLigence Real Time Cellular Analysis

2) *Pathway Specific Signaling*
Calcium signalling ($[Ca^{2+}]_i$)
Digital imaging microscopy
MAPK signaling
Traditional pERK/tERK Western blots
High Capacity In Cell Western

- The xCELLigence real time cell analyzer (RTCA) detects changes in adherent cell adhesion, morphology and viability over time by measuring impedance changes over time
- RTCA allows for high capacity (6x96 well plate) analysis of $PAR_2$ agonist response in a single experiment

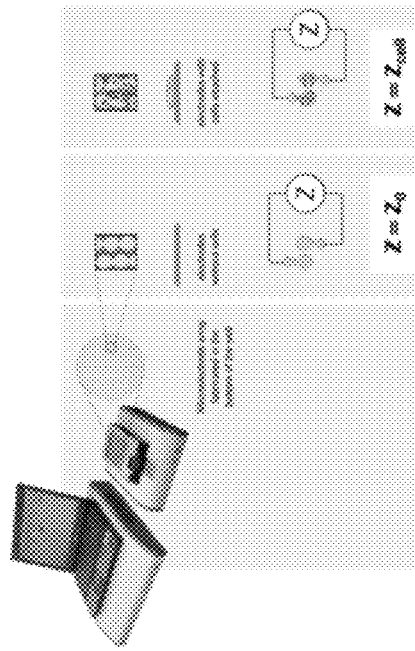

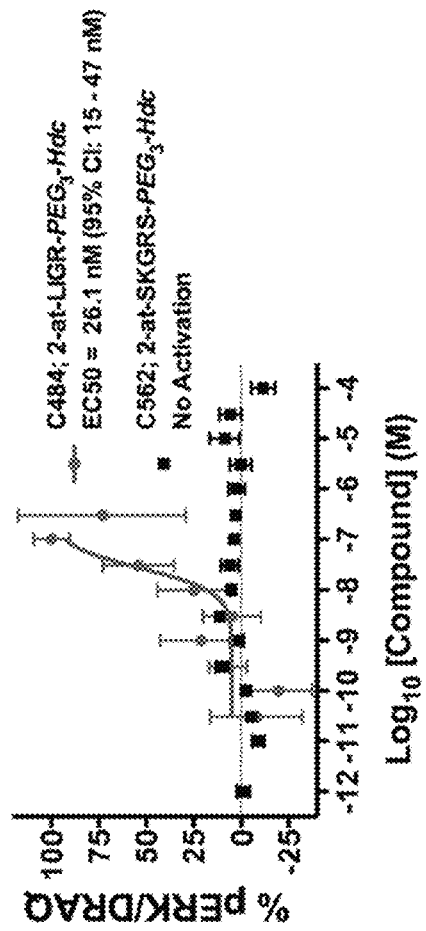
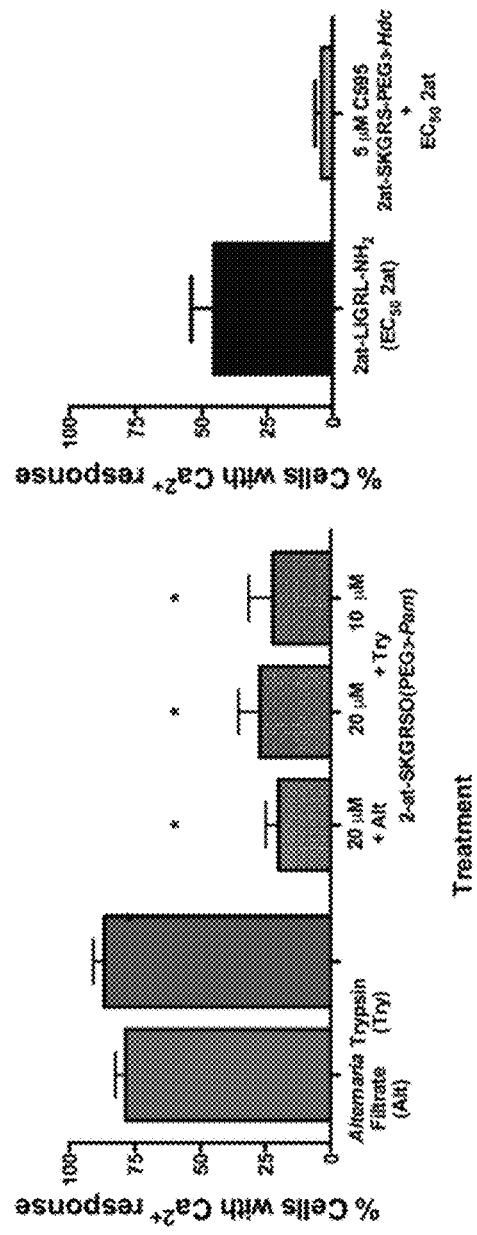
FIG. 4B

FIG. 5A

| Compound | Tethered Sequence | RTCA xCELLigence Response |
|---|---|---|
| C592 | 2-at-SKGR-*PEG3-Hdc* | PAR2 Antagonist |
| C595 | 2-at-SNGR-*PEG3-Hdc* | Positive PAR2 Allosteric Control |
| C596 | 2-at-SRGR-*PEG3-Hdc* | No Activity at PAR2 Detected |
| C597 | 2-at-SHGR-*PEG3-Hdc* | No Activity at PAR2 Detected |
| C598 | 2-at-SQGR-*PEG3-Hdc* | Positive PAR2 Allosteric Control |
| C599 | 2-at-TKGR-*PEG3-Hdc* | No Activity at PAR2 Detected |
| C605 | 2-at-LKGR-*PEG3-*Hdc | Full PAR2 Agonist |
| C556 | 2-at-IIGR-*PEG3-Hdc* | Full PAR2 Agonist |
| C607 | 2-at-SIGR-*PEG3-Hdc* | No Activity at PAR2 Detected |
| C608 | 2-at-TIGR-*PEG3-Hdc* | PAR2 Agonist and Antagonist |
| C674 | 2-at-DIGR-*PEG3-Hdc* | No Activity at PAR2 Detected |
| C675 | 2-at-HIGR-*PEG3-Hdc* | PAR2 Agonist |
| C676 | 2-at-NIGR-*PEG3-Hdc* | PAR2 Agonist |
| C670 | 2-at-hydroxyproline-IGR-*PEG3-Hdc* | No Activity at PAR2 Detected |
| C671 | 2-at-homoserine-IGR-*PEG3-Hdc* | PAR2 Agonist |
| C672 | 2-at-penicillamine-IGR-*PEG3-Hdc* | No Activity at PAR2 Detected |
| C673 | 2-at-4thiazolamine-IGR-*PEG3-Hdc* | No Activity at PAR2 Detected |
| C678 | 2-at-(dL)IGR-*PEG3-Hdc* | No Activity at PAR2 Detected |
| C679 | 2-at-(dI)IGR-*PEG3-Hdc* | No Activity at PAR2 Detected |
| C677 | 2-at-(dT)IGR-*PEG3-Hdc* | No Activity at PAR2 Detected |

SEQUENCE LISTING

```
<160> NUMBER OF SEQ ID NOS: 23

<210> SEQ ID NO 1
<211> LENGTH: 4
<212> TYPE: PRT
<213> ORGANISM: Artificial sequence
<220> FEATURE:
<223> OTHER INFORMATION: Synthetic

<400> SEQUENCE: 1

Leu Ile Gly Arg
1

<210> SEQ ID NO 2
<211> LENGTH: 4
<212> TYPE: PRT
<213> ORGANISM: Artificial sequence
<220> FEATURE:
<223> OTHER INFORMATION: Synthetic

<400> SEQUENCE: 2

Ser Leu Ile Gly
1

<210> SEQ ID NO 3
<211> LENGTH: 5
<212> TYPE: PRT
<213> ORGANISM: Artificial sequence
<220> FEATURE:
<223> OTHER INFORMATION: Synthetic

<400> SEQUENCE: 3

Ser Leu Ile Gly Arg
1               5

<210> SEQ ID NO 4
<211> LENGTH: 4
```

```
<212> TYPE: PRT
<213> ORGANISM: Artificial sequence
<220> FEATURE:
<223> OTHER INFORMATION: Synthetic

<400> SEQUENCE: 4

Thr Ile Gly Arg
1

<210> SEQ ID NO 5
<211> LENGTH: 5
<212> TYPE: PRT
<213> ORGANISM: Artificial sequence
<220> FEATURE:
<223> OTHER INFORMATION: Synthetic

<400> SEQUENCE: 5

Ser Lys Gly Arg Ser
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic

<400> SEQUENCE: 6

Ser Lys Gly Arg
1

<210> SEQ ID NO 7
<211> LENGTH: 4
<212> TYPE: PRT
<213> ORGANISM: Artificial sequence
<220> FEATURE:
<223> OTHER INFORMATION: Synthetic

<400> SEQUENCE: 7

His Ile Gly Arg
1

<210> SEQ ID NO 8
<211> LENGTH: 4
<212> TYPE: PRT
<213> ORGANISM: Artificial sequence
<220> FEATURE:
<223> OTHER INFORMATION: Synthetic

<400> SEQUENCE: 8

Val Ile Gly Arg
1

<210> SEQ ID NO 9
<211> LENGTH: 6
<212> TYPE: PRT
<213> ORGANISM: Artificial sequence
<220> FEATURE:
<223> OTHER INFORMATION: Synthetic

<400> SEQUENCE: 9

Ser Ser Lys Gly Arg Ser
1               5

<210> SEQ ID NO 10
<211> LENGTH: 5
<212> TYPE: PRT
```

```
<213> ORGANISM: Artificial sequence
<220> FEATURE:
<223> OTHER INFORMATION: Synthetic

<400> SEQUENCE: 10

Ser Lys Gly Arg Ser
1               5

<210> SEQ ID NO 11
<211> LENGTH: 4
<212> TYPE: PRT
<213> ORGANISM: Artificial sequence
<220> FEATURE:
<223> OTHER INFORMATION: Synthetic

<400> SEQUENCE: 11

Ser Arg Gly Arg
1

<210> SEQ ID NO 12
<211> LENGTH: 4
<212> TYPE: PRT
<213> ORGANISM: Artificial sequence
<220> FEATURE:
<223> OTHER INFORMATION: Synthetic

<400> SEQUENCE: 12

Ser His Gly Arg
1

<210> SEQ ID NO 13
<211> LENGTH: 4
<212> TYPE: PRT
<213> ORGANISM: Artificial sequence
<220> FEATURE:
<223> OTHER INFORMATION: Synthetic

<400> SEQUENCE: 13

Thr Lys Gly Arg
1

<210> SEQ ID NO 14
<211> LENGTH: 4
<212> TYPE: PRT
<213> ORGANISM: Artificial sequence
<220> FEATURE:
<223> OTHER INFORMATION: Synthetic

<400> SEQUENCE: 14

Leu Lys Gly Arg
1

<210> SEQ ID NO 15
<211> LENGTH: 4
<212> TYPE: PRT
<213> ORGANISM: Artificial sequence
<220> FEATURE:
<223> OTHER INFORMATION: Synthetic

<400> SEQUENCE: 15

Ser Ile Gly Arg
1

<210> SEQ ID NO 16
<211> LENGTH: 4
<212> TYPE: PRT
<213> ORGANISM: Artificial sequence
```

```
<220> FEATURE:
<223> OTHER INFORMATION: Synthetic

<400> SEQUENCE: 16

Asp Ile Gly Arg
1

<210> SEQ ID NO 17
<211> LENGTH: 5
<212> TYPE: PRT
<213> ORGANISM: Artificial sequence
<220> FEATURE:
<223> OTHER INFORMATION: Synthetic

<400> SEQUENCE: 17

Thr Ile Gly Arg Leu
1               5

<210> SEQ ID NO 18
<211> LENGTH: 5
<212> TYPE: PRT
<213> ORGANISM: Artificial sequence
<220> FEATURE:
<223> OTHER INFORMATION: Synthetic

<400> SEQUENCE: 18

Leu Ile Gly Arg Leu
1               5

<210> SEQ ID NO 19
<211> LENGTH: 6
<212> TYPE: PRT
<213> ORGANISM: Artificial sequence
<220> FEATURE:
<223> OTHER INFORMATION: synthetic

<400> SEQUENCE: 19

Ser Leu Ile Gly Arg Leu
1               5

<210> SEQ ID NO 20
<211> LENGTH: 6
<212> TYPE: PRT
<213> ORGANISM: Artificial sequence
<220> FEATURE:
<223> OTHER INFORMATION: synthetic

<400> SEQUENCE: 20

Ser Leu Ile Gly Lys Val
1               5

<210> SEQ ID NO 21
<211> LENGTH: 74
<212> TYPE: PRT
<213> ORGANISM: Artificial sequence
<220> FEATURE:
<223> OTHER INFORMATION: synthetic

<400> SEQUENCE: 21

Thr Thr Leu Lys Gly Thr Thr Val Ser Ala Ser Phe Glu Asp Val Ser
1               5                   10                  15

Phe Val Thr Glu Val Thr Gly Lys Gly Thr Val His Ser Thr Gly Asp
                20                  25                  30

Val Lys Gly Ile Leu Ser Arg Gly Lys Ser Ser Arg Asn Thr Gly Gln
            35                  40                  45
```

```
Ile Thr Gly Ser Cys Ser Leu Ser Ala Ala Leu Leu Ile Ala Ala Gly
 50                  55                  60

Leu Leu Trp Ala Ala Ser Pro Ser Arg Met
 65                  70

<210> SEQ ID NO 22
<211> LENGTH: 4
<212> TYPE: PRT
<213> ORGANISM: Artificial sequence
<220> FEATURE:
<223> OTHER INFORMATION: synthetic

<400> SEQUENCE: 22

Ser Lys Gly Ser
1

<210> SEQ ID NO 23
<211> LENGTH: 4
<212> TYPE: PRT
<213> ORGANISM: Artificial sequence
<220> FEATURE:
<223> OTHER INFORMATION: synthetic

<400> SEQUENCE: 23

Ser Lys Arg Ser
1
```

PAR2 MIMETIC PEPTIDES AND USES THEREOF

CROSS REFERENCE TO RELATED APPLICATION

The present application is a U.S. 371 national phase entry of International Patent Application No. PCT/US2017/025511, filed Mar. 31, 2017, which claims priority to U.S. Provisional Patent Application Ser. No. 62/317,305, filed Apr. 1, 2016, the disclosure of which is herein incorporated by reference in their entireties.

STATEMENT REGARDING FEDERALLY SPONSORED RESEARCH OR DEVELOPMENT

This invention was made with government support under Grant No. R01 NS073664 awarded by NIH. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,000 byte ASCII (Text) file named "33999_Replacement_ST25.txt." created on Aug. 12, 2021.

FIELD OF THE INVENTION

This invention is in the field of medicinal pharmacology. In particular, the invention relates to protease activated receptor type 2 ($PAR_2$) modulating compounds (e.g., mimetic peptides), compositions comprising such modulating compounds, and their use as therapeutics for the treatment of conditions involving $PAR_2$ activity.

INTRODUCTION

Chronic pain is a neurological disorder that impacts the lives of millions of Americans. Current treatments for chronic pain are limited by abuse potential and intolerable side effects. Endogenous proteases contribute to acute and chronic pain through the direct activation of the protease activated receptor-2 ($PAR_2$) G-protein coupled receptor (GPCR). $PAR_2$ is known to play an important role in chemical, inflammatory and cancer-induced pain but the possible efficacy of $PAR_2$ antagonists in these preclinical models has not been assessed due to lack of available tools or clinical candidate compounds. Moreover, activation of $PAR_2$ can lead to engagement of multiple signalling pathways yet agonists/antagonists with signalling pathway specific efficacy have not been explored as potential tools for understanding the role of $PAR_2$ signalling in nociception.

Asthma is a growing and potentially debilitating disease in the industrialized world. Available treatments for asthma have remained constant and novel approaches to therapies are needed. Cellular and animal studies have uncovered prominent roles for airway epithelial $PAR_2$ in detrimental inflammatory cytokine release and protective ecaisonoid release in response to allergic asthma. These apparently opposing responses can be targeted with novel compounds that individually or collectively modulate the multiple signalling pathways associated with allergen-induced $PAR_2$ activation.

Migraine pain is a major clinical problem. Almost 15 percent of the global population is affected by migraines during their lifetimes (see, e.g., Vos, T., et al., Lancet, 2012. 380(9859): p. 2163-96), and there are over 36 million migraine sufferers in the US alone. Even with this significant number of patients, treatments for migraine pain remains little more effective than over-the-counter analgesics. Part of the problem is that migraine etiology is complex and not well understood. Unlike common headaches, migraines have a specific presentation in which a prodrome, aura, and postdrome may occur with the migraine pain lasting between 4 and 72 hours. Hypersensitivity to light and sound, cutaneous allodynia, nausea, and other sensory-motor irregularities are also common symptoms of migraines. It is widely accepted that the trigeminal sensory system, including durally-projecting trigeminal ganglion (TG) nociceptors, is responsible for the pain associated with migraines (see, e.g., Bernstein, C. and R. Burstein, Journal of clinical neurology, 2012. 8(2): p. 89-99; Levy, D., Headache, 2010. 50(5): p. 909-16). However, it is not understood how the nociceptive afferents from the trigeminal system are activated/sensitized during a migraine attack or where any insults may occur that trigger a migraine attack. It is considered likely that deep cephalic tissues such as the meninges, or possibly the calvarial periosteum, are the tissues involved in nociception during a migraine attack and both have been studied as such in animal models of migraine.

Previous work in the migraine field has shown that degranulation of mast cells in the meninges can release serine proteases which in turn activate PARs and that this response is able to activate dural afferents projecting in the trigeminal nerve (see, e.g., Zhang, X. C. and D. Levy, Cephalalgia, 2008. 28(3): p. 276-84). Zhang and Levy used single-unit recording electrophysiology to monitor neurons in the trigeminal ganglia of anesthetized rats and applied SLIGRL (SEQ ID NO: 19), a non-specific peptide activator of $PAR_2$, to the dura of these animals. SLIGRL (SEQ ID NO: 19), exposure resulted in activation and sensitization of TG neurons. This work potentially reveals an important neuro-immune relationship that can explain a wide variety of migraine etiologies since mast cell degranulation can result from cortical spreading depression (CSD), nitric oxide (NO) donors, calcitonin gene-related peptide (CGRP), and heightened stress, all of which are associated with migraine. However, the use of SLIGRL (SEQ ID NO: 19) is problematic as it also activates MrgprC11, a receptor that is expressed in DRG and TG neurons and contributes to sensory neuron sensitization, with overlapping potency and efficacy to SLIGRL (SEQ ID NO: 19) action at $PAR_2$ (see, e.g., Ramachandran, R. and M. D. Hollenberg, Br J Pharmacol, 2008. 153 Suppl 1: p. S263-82; Ossovskaya, V. S. and N. W. Bunnett, Physiol Rev, 2004. 84(2): p. 579-621; Boitano S, et al., Br J Pharmacol 172: 4535-4545, 2015).

Accordingly, improved methods for treating conditions involving aberrant $PAR_2$ activity, including chronic pain, asthma and migraine, are needed.

SUMMARY OF THE INVENTION

Protease-activated receptor type 2 ($PAR_2$) is a G-protein-coupled receptor (GPCR) implicated in disease conditions including allergic asthma (Br J Pharmacol 2009:158:1017-33), cancer (Scand J Gastroenterol 2008; 43:902-9) arthritis (Biol Chem 2008; 389:971-82), and chronic pain (Physiol Rev 2004; 84:579-621) $PAR_2$ can be activated in response to various exogenous and endogenous proteases (Br J Pharmacol 2008; 153(suppl 1):S263-282). Proteolytic cleavage of the N terminus results in exposure of a tethered ligand that activates the receptor to induce signalling (Physiol Rev 2004; 84:579-621). The primary method to study $PAR_2$ has been small peptides or peptidomimetics that mimic the naturally cleaved tethered ligand thus bypassing proteolytic cleavage of the N-terminal domain. This approach can be problematic, however, because this peptide sequence also activates mas-related G protein-coupled receptors (Mrgpr and GPCRs) that are specifically expressed in the sensory system and are involved in pain and itch signalling (Sci Signal 2011; 4:ra45). Although $PAR_2^{-/-}$ mice have been indispensable for elucidating the role of this receptor in normal physiology and pathology (Physiol Rev 2004; 84:579-621), a lack of suitable pharmacological tools have hindered full exploration of the role of this receptor in disease conditions, including chronic pain (Pharmacol Ther 2011; 130:248-82). Highly potent, efficacious, and specific agonists have been developed (J Med Chem 2011; 54:1308-13; J Biol Chem 2011; 286:19076-88; J Physiol 2007; 578:715-33) and used them in experiments to explore the role of $PAR_2$ in the development of a chronic pain state.

$PAR_2$ is thought to play an important role in inflammatory (Semin Thromb Hemost 2006; 32(suppl 1): 39-48; Physiol Rev 2004; 84:579-621; Nat Med 2001; 7:821-6), visceral (Gastroenterology 2011; 141:1864-74e1-3; J Clin Invest 2007; 117:636-47; Br J Pharmacol 2006; 148:54-60; PAIN 2014; 155:1328-38; Pancreas 2011; 40:300-7), and cancer-evoked (Mol Pain 2014; 10:28; J Neurosci 2012; 32:14178-83; PAIN 2010; 149: 263-72; Eur J Pain 2013; 18:326-37) pain based on studies using $PAR_2^{-/-}$ mice and/or antagonists suggesting an important role of $PAR_2$ in pathological pain. Hyperalgesic priming models have emerged as an important paradigm for probing plasticity associated with chronic pain in the nociceptive system (Trends Neurosci 2009; 32:611-18). It has been previously demonstrated that a single injection of interleukin-6 (IL-6) induces hyperalgesic priming and that this priming is dependent on plasticity in the peripheral and central nervous system (J Neurosci 2011; 31:6646-53; J Neurosci 2010; 30:15113-23; Mol Pain 2013; 9:12; Mol Pain 2014; 10:45). This is consistent with similar experiments in rats using inflammatory stimuli (Trends Neurosci 2009; 32:611-18). Importantly, $PAR_2^{-/-}$ mice fail to show nociceptive sensitization in many inflammatory pain models (Semin Thromb Hemost 2006; 32(suppl 1):39-48) and $PAR_2$ mediates alterations in dorsal root ganglion (DRG) BDNF levels (Mol Pain 2014; 10:28), a critical factor for hyperalgesic priming (Mol Pain 2013; 9:12; Mol Pain 2014; 10:45).

A central hypothesis for experiments conducted during the course of developing embodiments for the present invention was that $PAR_2$ plays a pivotal role in causing acute pain, promoting chronic pain, and in both promoting and controlling asthma symptoms, and that high affinity ligands of $PAR_2$ will represent a novel class of analgesics with utility in a number of chronic pain conditions and in the control of asthma. Thus, a primary objective of experiments conducted during the course of developing embodiments for the present invention was to develop novel and specific ligands to $PAR_2$, to fully elucidate $PAR_2$ contribution to acute and chronic pain and asthma, and to evaluate $PAR_2$ ligand efficacy as novel analgesics in preclinical pain and asthma models.

Accordingly, the present invention relates to modulating compounds that function as activators and inhibitors of $PAR_2$ proteins. The invention further relates to methods of treating, ameliorating, or preventing disorders in a patient, such as those that are responsive to either $PAR_2$ activation or $PAR_2$ inhibition, comprising administering to a subject (e.g., a human patient) a composition comprising one or more of the $PAR_2$ modulating compounds of the invention and, potentially, additional agent(s). Such disorders include those characterized by aberrant $PAR_2$ activity (e.g., inflammatory disorders such as asthma and chronic pain).

The present invention is not limited to particular types or kinds of modulating compounds that function as activators and inhibitors of $PAR_2$ proteins. In some embodiments, the modulating compounds include small molecule compounds and mimetic peptides.

In certain embodiments, the modulating compounds which function as activators and inhibitors of $PAR_2$ proteins are $PAR_2$ mimetic peptides. For example, in certain embodiments, the present invention provides compositions comprising a $PAR_2$ mimetic peptide. In some embodiments, the $PAR_2$ mimetic peptide is encompassed within Formula I:

[heterocycle moiety]-[peptide sequence]-[linker moiety]-[cell membrane anchoring moiety], including pharmaceutically acceptable salts, lipidated analogs, pegylated analogs, and/or prodrugs thereof. Such $PAR_2$ mimetic peptides are not limited to a particular heterocycle moiety. In some embodiments, the heterocycle moiety comprises at least one atom selected from Nitrogen, Oxygen and Sulfur. In some embodiments, the heterocycle moiety is selected from the group consisting of a thiazole moiety, a pyridine moiety, an azabicycloalkane moiety, an aminothiazoyl moiety, and an aminonicotinyl moiety.

Such $PAR_2$ mimetic peptides are not limited to a particular position for the heterocycle moiety. In some embodiments, the heterocycle moiety is positioned at the N-terminus of the $PAR_2$ mimetic peptide.

Such $PAR_2$ mimetic peptides are not limited to a particular peptide sequence. In some embodiments, the peptide sequence comprises two or more contiguous amino acid residues. In some embodiments, the two or more contiguous amino acid residues render the resulting $PAR_2$ mimetic peptide as a $PAR_2$ activator and/or a $PAR_2$ inhibitor. In some embodiments, the amino acid sequence selected from the group consisting of Ile-Gly, Ile-Gly-Arg, Leu-Ile-Gly, Leu-Ile-Gly, Leu-Ile-Gly-Arg (SEQ ID NO:1), Ser-Leu-Ile-Gly (SEQ ID NO:2), Ser-Leu-Ile-Gly-Arg (SEQ ID NO:3), Thr-Ile-Gly, Thr-Ile-Gly-Arg (SEQ ID NO:4), Ser-Lys-Gly-Arg-Ser (SEQ ID NO:5), Ser-Lys-Gly-Arg (SEQ ID NO:6), His-Ile-Gly-Arg (SEQ ID NO:7), Val-Ile-Gly-Arg (SEQ ID NO:8), any of the peptide sequences described in Example 1, and any of the peptide sequences described in Tables 1, 2, 3, 4 and 5.

Such $PAR_2$ mimetic peptides are not limited to a particular linker moiety. In some embodiments, the linker moiety comprises a chemical moiety configured to bridge the peptide sequence and cell membrane anchoring moiety. In some embodiments, the linker moiety comprises a chemical moiety selected from the group consisting of a substituted aliphatic chain, an unsubstituted aliphatic chain, substituted aromatic moiety, an unsubstituted aromatic moiety, a linear polymer, one or more polyethylene glycol (PEG) moieties, one or more 3,19-dioxo-2,8,11,14,21-pentaoxa-4,18-diazatricosan-23-oic acid residue derivative moieties, and/or any combination thereof. In some embodiments, the linker moiety comprises a polyethylene glycol (PEG) moiety. In some embodiments, the linker moiety comprises multimers of 3,19-dioxo-2,8,11,14,21-pentaoxa-4,18-diazatricosan-23-oic acid. In some embodiments, the linker moiety comprises a polyethylene glycol (PEG) moiety. In some embodiments, the linker moiety is a linear polymer comprising monomeric subunits. In some embodiments, the linear polymer comprises saccharide moieties, peptide moieties, lactone moieties, acrylate moieties, and/or synthetic polymer moieties. In some embodiments, the linear polymer comprises collagen-like polypeptides and/or synthetic surrogates of spider silk.

Such $PAR_2$ mimetic peptides are not limited to a particular cell membrane anchoring moiety. In some embodiments, the cell membrane anchoring moiety comprises a hydrophobic chemical moiety or a synthetic structure that forms a non-covalent binding interaction with a cell membrane.

Such $PAR_2$ mimetic peptides are not limited to a particular position for the cell membrane anchoring moiety. In some embodiments, the cell membrane anchoring moiety is positioned at the C-terminus of the $PAR_2$ mimetic peptide. In some embodiments, the cell membrane anchoring moiety comprises a lipid moiety. In some embodiments, the cell membrane anchoring moiety comprises a saturated or unsaturated hydrocarbon moiety. In some embodiments, the cell membrane anchoring moiety is hexadecyl. In some embodiments, the cell membrane anchoring moiety is a saturated $C_{12}$-$C_{20}$ alkyl residue. In some embodiments, the cell membrane anchoring moiety is a cell membrane homing structure. In some embodiments, the cell membrane anchoring moiety is a cell-penetrating moiety. In some embodiments, the cell membrane anchoring moiety is a transmembrane domain.

In some embodiments, the $PAR_2$ mimetic peptide is configured to modulate $PAR_2$ biological activity. For example, in some embodiments, the $PAR_2$ mimetic peptide is configured to activate $PAR_2$ biological activity. In some such embodiments, the mimetic peptide is: [2-aminothiazoyl]-[LIGR (SEQ ID NO:1)]-[$PEG_3$]-[hexadecyl]. In some such embodiments, the mimetic peptide is: [2-aminothiazoyl]-[HIGR (SEQ ID NO:7)]-[$PEG_3$]-[hexadecyl]. In some such embodiments, the mimetic peptide is: [2-aminothiazoyl]-[VIGR (SEQ ID NO: 8)]-[$PEG_3$]-[hexadecyl]. In some such embodiments, the mimetic peptide is: [2-aminothiazoyl]-[(homoserine)IGR]-[$PEG_3$]-[hexadecyl].

In some embodiments, the $PAR_2$ mimetic peptide is configured to antagonize $PAR_2$ biological activity.

In some such embodiments, the mimetic peptide is configured to antagonize $PAR_2$ activity resulting from interaction between trypsin and $PAR_2$. In some such embodiments, the mimetic peptide is: [2-aminothiazoyl]-[Thr-Ile-Gly-Arg (SEQ ID NO:4)]-[$PEG_3$]-[hexadecyl].

In some embodiments, the mimetic peptide is configured to antagonize $PAR_2$ activity resulting from interaction between kallikrein 5 and $PAR_2$. In some such embodiments, the mimetic peptide is: [2-aminothiazoyl]-[Ser-Lys-Gly-Arg-Ser (SEQ ID NO:5)]-[$PEG_3$]-[hexadecyl]. In some such embodiments, the mimetic peptide is: [2-aminothiazoyl]-[Ser-Lys-Gly-Arg (SEQ ID NO:6)]-[$PEG_3$]-[hexadecyl].

In some such embodiments, the mimetic peptide is: [2-aminothiazol-4yl]-[SKGRS (SEQ ID NO:10)]-[$PEG_3$]-[Hdc].

In some such embodiments, the mimetic peptide is: [2-aminothiazol-4yl]-[SKGR (SEQ ID NO:6)]-[$PEG_3$]-[Hdc].

In some such embodiments, the mimetic peptide is: [2-aminothiazol-4yl]-[LIGR (SEQ ID NO:1)]-[$PEG_3$]-[Hdc].

In some such embodiments, the mimetic peptide is: [2-aminothiazol-4yl]-[TIGR (SEQ ID NO: 4)]-[$PEG_3$]-[Hdc].

In some such embodiments, the mimetic peptide is shown in Tables 1, 2, 3, 4, and/or 5.

In some embodiments, the mimetic peptide is 2-at-LIGRL (SEQ ID NO:18)-$PEG_3$-Hdc (

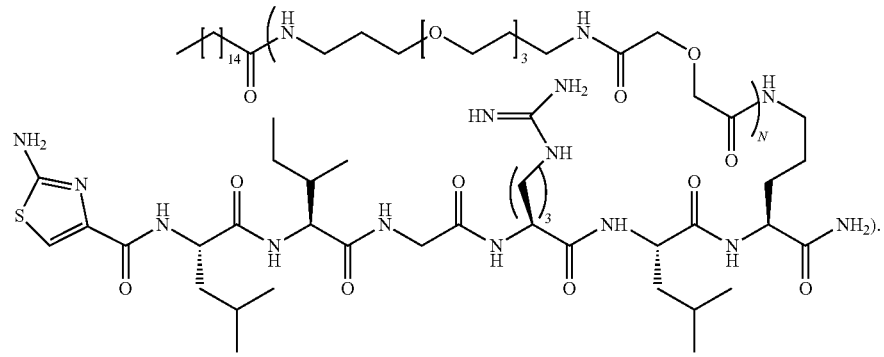

).

In certain embodiments, the modulating compounds which function as activators and inhibitors of $PAR_2$ proteins are small molecules. For example, in some embodiments the present invention provides small molecule compounds encompassed within Formula II:

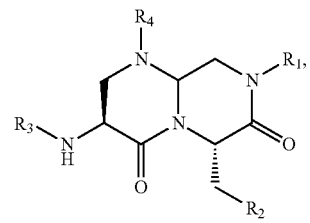

including pharmaceutically acceptable salts, solvates, and/or prodrugs thereof.

Formula I is not limited to a particular chemical moiety for $R_1$, $R_2$, $R_3$, and $R_4$. In some embodiments, the particular chemical moiety for $R_1$, $R_2$, $R_3$, and $R_4$ independently include any chemical moiety that permits the resulting compound to function as an inhibitor of $PAR_2$ protein activity. In some embodiments, the particular chemical moiety for $R_1$, $R_2$, $R_3$, and $R_4$ independently include any chemical moiety that permits the resulting compound to function as an activator of $PAR_2$ protein activity.

Such compounds are not limited to a particular chemical moiety for $R_1$. In some embodiments, $R_1$ is selected from

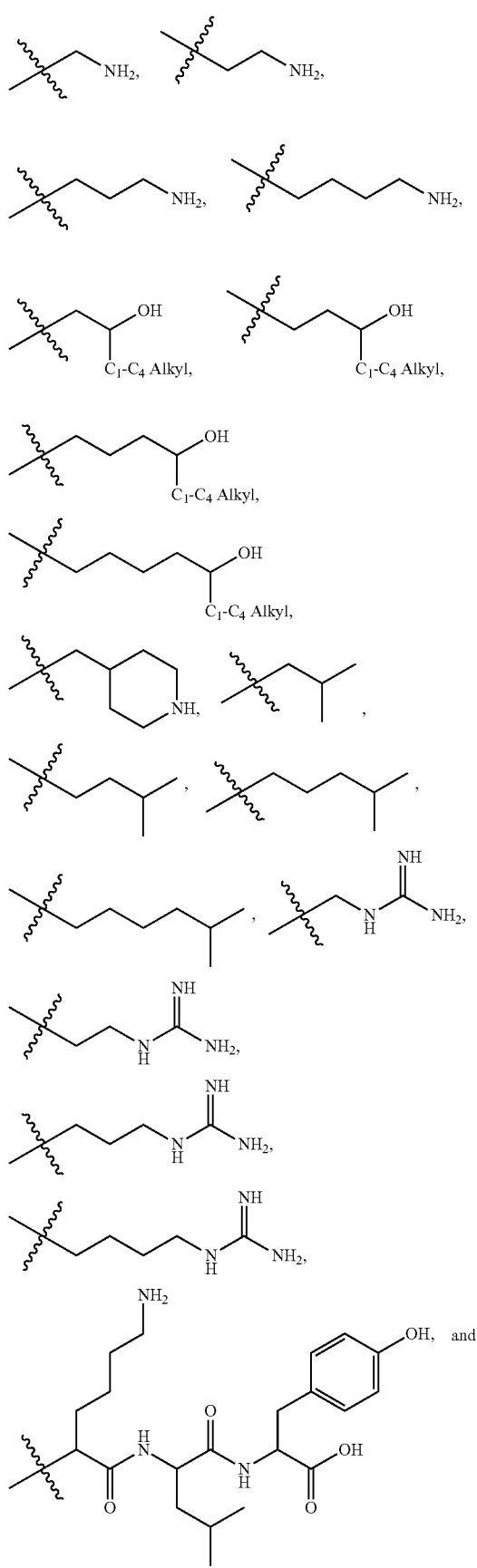
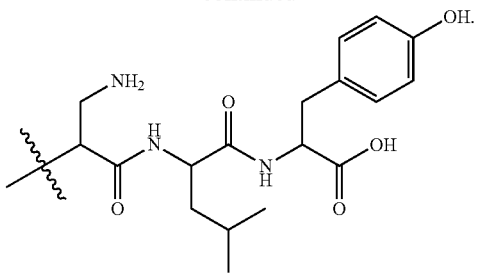
In some embodiments, R₂ is an amino acid selected from a Leu, Ile, Val, Cha, Arg, Orn, Lys, Dap, Thr, Ser, and Tyr.
In some embodiments, R₃ is selected from 2-furoyl
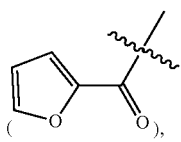
acetyl
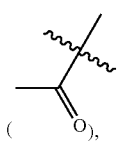 [SMILES: *C(C)=O]
3-methylbutyryl
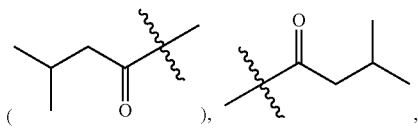
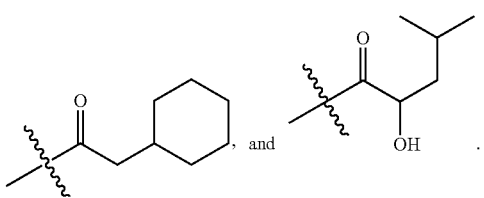
In some embodiments, R₄ is selected from 2-furoyl
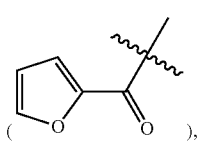

acetyl

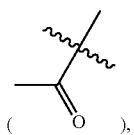
( ), 3-methylbutyryl

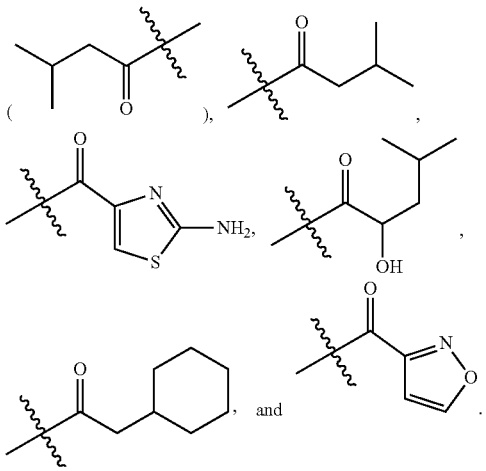
, and .

In certain embodiments, the modulating compound is the PAR$_2$ antagonist C391

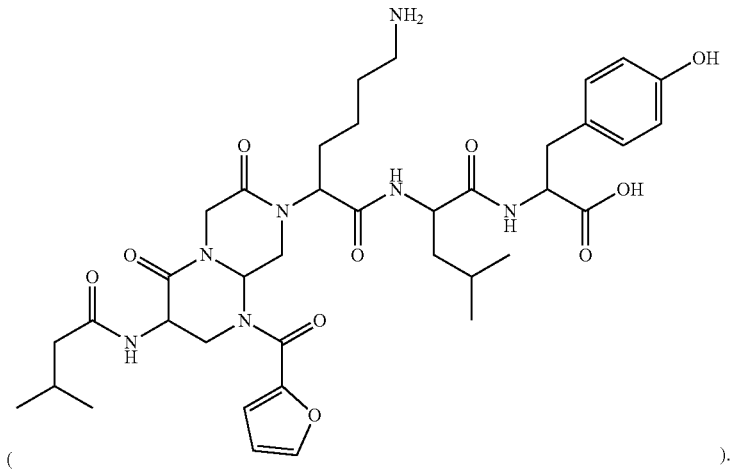 [SMILES: CC(C)CC(=O)NC1CN(C(=O)c2ccco2)C2CN(C(CCCCN)C(=O)NC(CC(C)C)C(=O)NC(Cc3ccc(O)cc3)C(=O)O)C(=O)CN2C1=O]
( ).

In some embodiments, the C391 is lipidated.

In certain embodiments, the present invention provides methods for modulating the activity of PAR$_2$ in a subject (e.g., human subject, non-human subject), comprising administering to the subject a PAR$_2$ modulating compound as described herein (e.g., a mimetic peptide, a small molecule) of the present invention. In some embodiments, the subject is experiencing aberrant PAR$_2$ activity. In some embodiments, the subject is at risk for experiencing aberrant PAR$_2$ activity. In some embodiments, the subject has or is at risk for developing an inflammatory condition (e.g., asthma) involving aberrant PAR$_2$ activity. In some embodiments, the subject has or is at risk for developing chronic pain involving aberrant PAR$_2$ activity.

In some embodiments, the inflammatory condition is one or more conditions selected from the group consisting of asthma, chronic pain, cancer, and a vascular disorder.

In some embodiments, the methods further comprise administering to the subject one or more additional agents (e.g., anti-inflammatory agents, anti-cancer agents, pain-relieving agents). In some embodiments, the additional agent is an anti-inflammatory agent. In some embodiments, the anti-inflammatory agent is a non-steroidal anti-inflammatory drug. In some embodiments, anti-inflammatory agent is albuterol.

In certain embodiments, the pharmaceutical composition comprises a PAR$_2$ mimetic peptide of the present invention and a pharmaceutically acceptable carrier.

In certain embodiments, the present invention provides kits comprising a pharmaceutical composition comprising a PAR$_2$ mimetic peptide of the

BRIEF DESCRIPTION OF THE DRAWINGS

FIGS. 4A-C show PAR$_2$ tethered ligand probe development—kallikrein site.

FIGS. 5A-B show in vitro physiological PAR$_2$ agonist screening using xCELLigence.

DETAILED DESCRIPTION OF THE INVENTION

Figure 1:
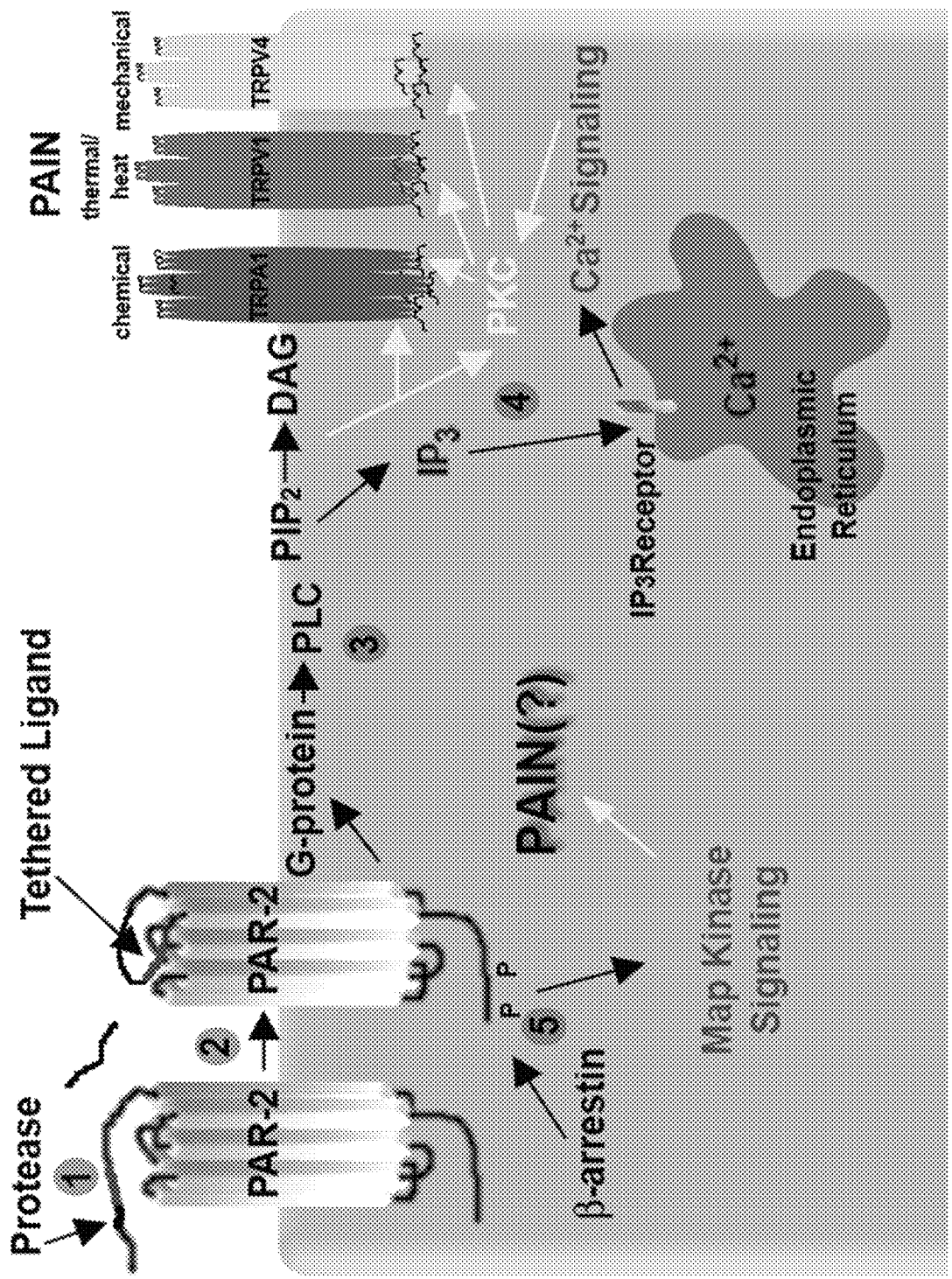
FIG. 1 shows the primary PAR$_2$ signalling pathways.

The protease-activated receptor-2 (PAR$_2$) is one of the four members of the family of GPCRs that are activated after proteolytic cleavage of their extracellular, amino terminus (Adams et al., Pharmacol. Ther. 130, 248-282; Ramachandran, R., et al., (2012) Nat. Rev. Drug Discov. 11, 69-86). The resulting 'tethered-peptide' sequence (ending with SLIGRL (SEQ ID NO: 19) in the rodent receptor and SLIGKV (SEQ ID NO: 20) in the human receptor) exposed after proteolytic cleavage activates PAR$_2$. A variety of potent and effective peptidomimetic agonists based upon the exposed tethered sequences have been developed to PAR$_2$ (Adams et al., Pharmacol. Ther. 130, 248-282; Boitano S, et al. (2014) PLoS ONE 9: e99140). These compounds have been very useful in understanding the consequences of PAR$_2$ activation across experimental models. However, the natural tethered agonist presentation for PAR$_2$, and its corresponding access to the PAR$_2$ binding pocket, has proved a difficult target for development of antagonists. Despite this difficulty, a number of PAR$_2$ antagonists have been proposed (Suen J Y, et al., (2012) Br J Pharmacol 165:1413-1423; Yau M K, et al., (2013) J Med Chem 56: 7477-7497). Further complicating the issue of drug development is the growing evidence for 'biased signalling' that can follow PAR$_2$ agonism (Hollenberg, M. D., et al., 2014. 171(5): p. 1180-94) or antagonism (Goh, F. G., et al., British journal of pharmacology, 2009. 158(7): p. 1695-704; Suen, J. Y., et al., 2014. 171(17): p. 4112-24).

PAR$_2$ plays an important role in a variety of diseases linked to proteinase release from endogenous sources or exposure to exogenous proteinases (Ramachandran R, et al., (2012) Nat Rev Drug Discov 11: 69-86, Hollenberg, M. D., et al., 2014. 171(5): p. 1180-94). One consequence of PAR$_2$ activation in the peripheral nervous system is sensitization of neurons responsible for transmitting noxious information to the CNS. These nociceptive neurons express PAR$_2$, and PAR$_2$ activation on these neurons leads to enhanced signalling via a variety of channels including the capsaicin and noxious heat receptor, TRPV1 (Dai Y, et al., (2004) J Neurosci 24: 4293-4299). PAR$_2$ is responsible for proteinase sensitization of TRPV1 in vivo, leading to thermal hyperalgesia. PAR$_2$ null animals have deficits in pain sensitization in a variety of inflammatory pain models, and PAR$_2$ activation is sufficient to induce a transition to a chronic pain state, making this receptor an important target for drug development for pathological pain (Vergnolle N (2009) Pharmacol Ther 123: 292-309; Bao Y, et al., 2014 Expert Opin Ther Targets 18: 15-27; Tillu D V, et al. (2015) Pain 156: 859-867). Additionally, a broad variety of preclinical and clinical findings link exogenous proteinases, and more specifically PAR$_2$, to asthma (Reed C E, Kita H (2004) J Allergy Clin Immunol 114: 997-1008, quiz 1009; Vergnolle N (2009) Pharmacol Ther 123: 292-309; Jacquet A (2011) Clin Exp Allergy 41: 305-311; Snelgrove R J, et al., (2014) J Allergy Clin Immunol 134: 583-592). While there is a strong rationale for PAR$_2$ antagonist drug discovery for these indications, few PAR$_2$ antagonists have been described and even fewer have been demonstrated to exhibit efficacy in preclinical disease models (Yau, M. K., et al., J Med Chem, 2013. 56(19): p. 7477-97).

The present invention provides PAR$_2$ mimetic peptides that utilize this ligand chemistry combined with alternative PAR$_2$ cleavage sites. Indeed, experiments conducted during the course of developing embodiments for the present invention identified highly potent PAR$_2$ peptides and mimetic activators and agonists.

Accordingly, the present invention relates to modulating compounds which function as activators and inhibitors of PAR$_2$ proteins. The invention further relates to methods of treating, ameliorating, or preventing disorders in a patient, such as those that are responsive to either PAR$_2$ activation or PAR$_2$ inhibition, comprising administering to a subject (e.g., a human patient) a composition comprising one or more of the PAR$_2$ mimetic peptides off the invention and, potentially, additional agent(s). Such disorders include those characterized by aberrant PAR$_2$ activity (e.g., inflammatory disorders).

In a particular embodiment, modulating compounds include mimetic peptides which function as activators and inhibitors of PAR$_2$ proteins. Indeed, in some embodiments, the present invention provides PAR$_2$ mimetic peptides having Formula I:

[heterocycle moiety]-[peptide sequence]-[linker moiety]-[cell membrane anchoring moiety], including pharmaceutically acceptable salts, lipidated analogs, pegylated analogs, and/or prodrugs thereof.

Formula I is not limited to particular chemical moieties for the heterocyle moiety, the peptide sequence, the linker moiety, and/or the cell membrane anchoring moiety.

In some embodiments, the heterocycle moiety is any aromatic heterocycle moiety that comprises at least one atom selected from Nitrogen, Oxygen and Sulfur. Examples of such heterocyle moieties include, but are not limited to, a thiazole moiety, a pyridine moiety, an azabicycloalkane moiety, an aminothiazoyl moiety, and/or an aminonicotinyl moiety.

The heterocyle moiety is not limited to a particular positioning within the PAR$_2$ mimetic peptide. In some embodiments, the aromatic heterocycle moiety is positioned at the N-terminus of the PAR$_2$ mimetic peptide.

In some embodiments, the peptide sequence is any peptide sequence that comprises two or more contiguous amino acid residues. In some embodiments, the peptide sequence is any combination of two or more contiguous amino acid residues that confers PAR$_2$ activating properties or PAR$_2$ antagonizing properties onto the PAR$_2$ mimetic peptide. Examples of the two or more contiguous amino acid residues include, but are not limited to Ile-Gly, Ile-Gly-Arg, Leu-Ile-Gly, Leu-Ile-Gly, Leu-Ile-Gly-Arg (SEQ ID NO:1), Ser-Leu-Ile-Gly (SEQ ID NO:2), Ser-Leu-Ile-Gly-Arg (SEQ ID NO:3), Thr-Ile-Gly, Thr-Ile-Gly-Arg (SEQ ID NO:4), Ser-Lys-Gly-Arg-Ser (SEQ ID NO:5), SKGR (SEQ ID NO:6), HIGR (SEQ ID NO:7), VIGR (SEQ ID NO:8), any of the peptide sequences described in Example 1, and any of the peptide sequences described in Tables 1, 2, 3, 4 and 5.

In some embodiments, the linker moiety is a chemical moiety configured to bridge the peptide sequence and cell membrane anchoring moiety. Examples of such linker moieties include, but are not limited to, a substituted aliphatic chain, an unsubstituted aliphatic chain, substituted aromatic chain, an unsubstituted aromatic chain, a linear polymer, one or more polyethylene glycol (PEG) moieties, one or more 3,19-dioxo-2,8,11,14,21-pentaoxa-4,18-diazatricosan-23-oic acid residue derivative moieties, and/or any combination thereof. In some embodiments, the linker moiety comprises a polyethylene glycol (PEG) moiety. In some embodiments, the linker moiety comprises multimers of 3,19-dioxo-2,8, 11,14,21-pentaoxa-4,18-diazatricosan-23-oic acid.

In some embodiments, the linker moiety is a linear polymer that comprises monomeric subunits. For example, in some embodiments, the linear polymer comprises saccharide moieties, peptide moieties, lactone moieties, acrylate moieties, and/or synthetic polymer moieties. In some embodiments, the linear polymer comprises collagen-like polypeptides and/or synthetic surrogates of spider silk.

In some embodiments, the cell membrane anchoring moiety is any chemical moiety that comprises a hydrophobic chemical moiety or a synthetic structure that forms a non-covalent binding interaction with a cell membrane. The PAR$_2$ mimetic peptides are not limited to a particular type or kind of a cell membrane anchoring moiety. In some embodiments, cell membrane moiety comprises a lipid moiety. In some embodiments, the cell membrane anchoring moiety comprises a saturated or unsaturated hydrocarbon moiety. In some embodiments, the cell membrane anchoring moiety is hexadecyl. In some embodiments, the cell membrane anchoring moiety is a saturated $C_{12}$-$C_{20}$ alkyl residue. In some embodiments, the cell membrane anchoring moiety is a cell-penetrating moiety. In some embodiments, the cell membrane anchoring moiety is a transmembrane domain.

between kallikrein 5 and PAR$_2$. In some such embodiments, the mimetic peptide is: [2-aminothiazoyl]-[Ser-Lys-Gly-Arg-Ser (SEQ ID NO:5)]-[PEG$_3$]-[hexadecyl]. In some such embodiments, the mimetic peptide is: [2-aminothiazoyl]-[Ser-Lys-Gly-Arg (SEQ ID NO:6)]-[PEG$_3$]-[hexadecyl].

In some such embodiments, the mimetic peptide is: [2-aminothiazol-4yl]-[SKGRS (SEQ ID NO:10)]-[PEG$_3$]-[Hdc].

In some such embodiments, the mimetic peptide is: [2-aminothiazol-4yl]-[SKGR (SEQ ID NO:6)]-[PEG$_3$]-[Hdc].

In some such embodiments, the mimetic peptide is: [2-aminothiazol-4yl]-[LIGR (SEQ ID NO:1)]-[PEG$_3$]-[Hdc].

In some such embodiments, the mimetic peptide is: [2-aminothiazol-4yl]-[TIGR (SEQ ID NO: 4)]-[PEG$_3$]-[Hdc].

In some such embodiments, the mimetic peptide is shown in Tables 1, 2, 3, 4, and/or 5.

In some embodiments, the mimetic peptide is 2-at-LIGRL (SEQ ID NO:18)-PEG$_3$-Hdc

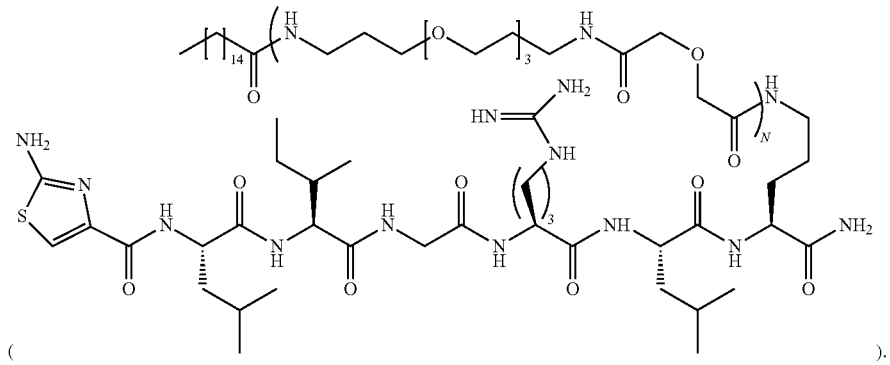

(

).

The cell membrane anchoring moiety is not limited to a particular positioning within the PAR$_2$ mimetic peptide. In some embodiments, the cell membrane anchoring moiety is positioned at the C-terminus of the PAR$_2$ mimetic peptide.

In some embodiments, the length of the [linker moiety]-[cell membrane anchoring moiety] is approximately 30-50 Angstroms.

In some embodiments, the PAR$_2$ mimetic peptide is configured to modulate PAR$_2$ biological activity. For example, in some embodiments, the PAR$_2$ mimetic peptide is configured to activate PAR$_2$ biological activity. In some such embodiments, the mimetic peptide is: [2-aminothiazoyl]-[LIGR (SEQ ID NO:1)]-[PEG$_3$]-[hexadecyl]. In some such embodiments, the mimetic peptide is: [2-aminothiazoyl]-[HIGR (SEQ ID NO:7)]-[PEG$_3$]-[hexadecyl]. In some such embodiments, the mimetic peptide is: [2-aminothiazoyl]-[VIGR (SEQ ID NO:8)]-[PEG$_3$]-[hexadecyl]. In some such embodiments, the mimetic peptide is: [2-aminothiazoyl]-[(homoserine)IGR]-[PEG$_3$]-[hexadecyl].

In some embodiments, the PAR$_2$ mimetic peptide is configured to antagonize PAR$_2$ biological activity.

In some such embodiments, the mimetic peptide is configured to antagonize PAR$_2$ activity resulting from interaction between trypsin and PAR$_2$. In some such embodiments, the mimetic peptide is: [2-aminothiazoyl]-[Thr-Ile-Gly-Arg (SEQ ID NO:4)]-[PEG$_3$]-[hexadecyl].

In some embodiments, the mimetic peptide is configured to antagonize PAR$_2$ activity resulting from interaction In certain embodiments, the modulating compounds which function as activators and inhibitors of PAR$_2$ proteins are small molecules. For example, in some embodiments the present invention provides small molecule compounds encompassed within Formula I:

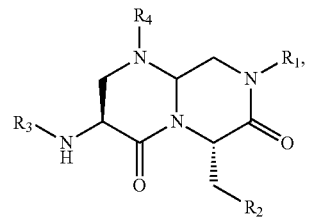

including pharmaceutically acceptable salts, solvates, and/or prodrugs thereof.

Formula I is not limited to a particular chemical moiety for $R_1$, $R_2$, $R_3$, and $R_4$. In some embodiments, the particular chemical moiety for $R_1$, $R_2$, $R_3$, and $R_4$ independently include any chemical moiety that permits the resulting compound to function as an inhibitor of PAR$_2$ protein activity. In some embodiments, the particular chemical moiety for $R_1$, $R_2$, $R_3$, and $R_4$ independently include any chemical moiety that permits the resulting compound to function as an activator of PAR$_2$ protein activity.

Such compounds are not limited to a particular chemical moiety for $R_1$. In some embodiments, $R_1$ is selected from
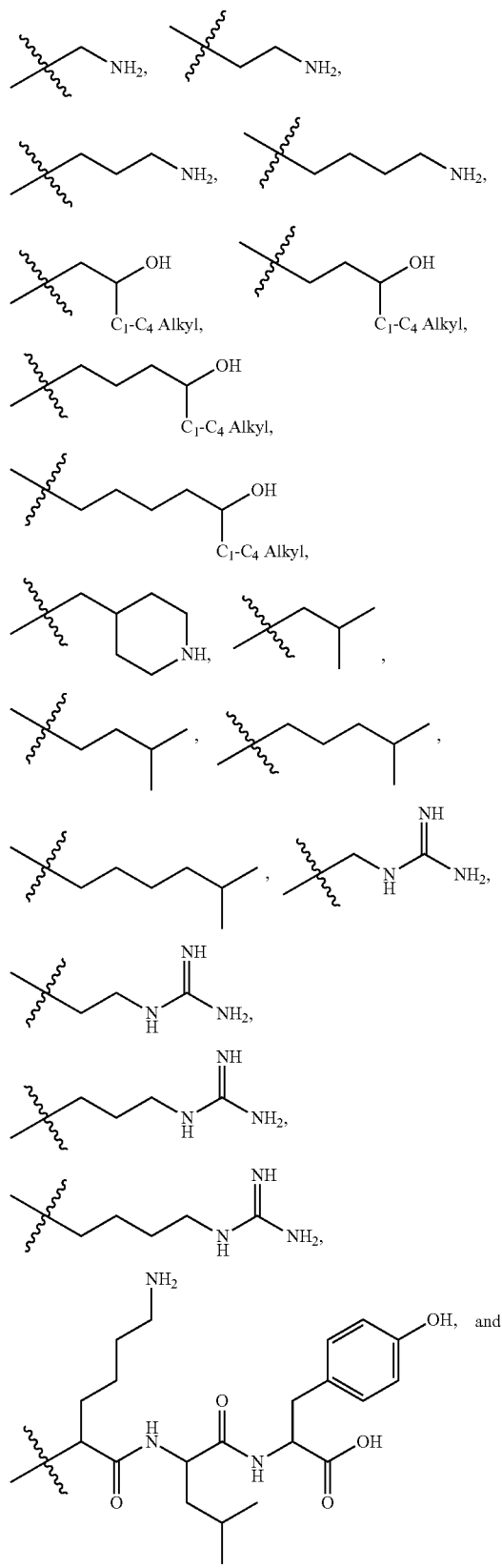
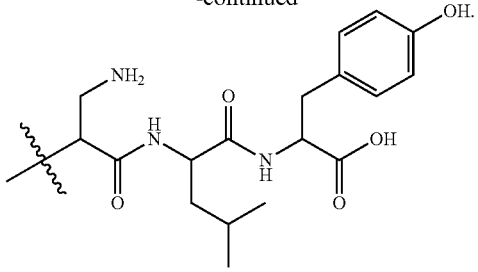
In some embodiments, $R_2$ is an amino acid selected from a Leu, Ile, Val, Cha, Arg, Orn, Lys, Dap, Thr, Ser, and Tyr.
In some embodiments, $R_3$ is selected from 2-furoyl
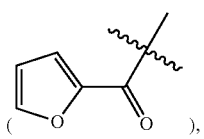
acetyl
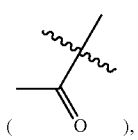
3-methylbutyryl
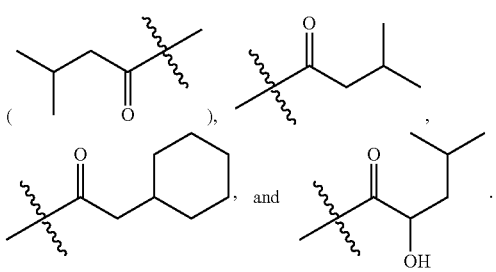
In some embodiments, $R_4$ is selected from 2-furoyl
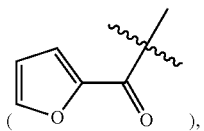
acetyl
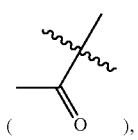

3-methylbutyryl

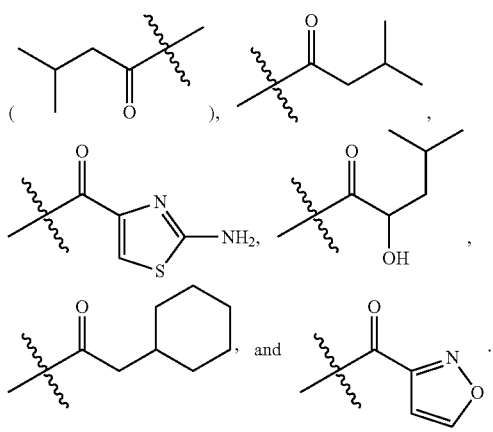

In certain embodiments, the modulating compound is the PAR$_2$ antagonist C391

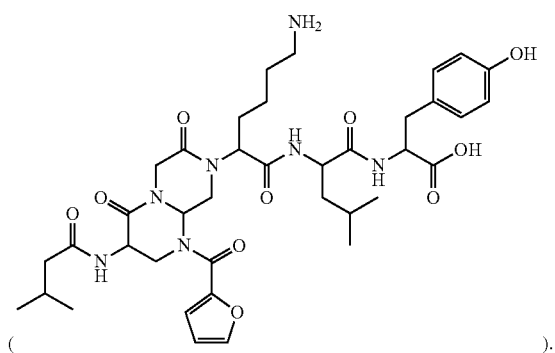 [SMILES: CC(C)CC(=O)NC1CN(C(=O)c2ccco2)C2CN(C(CCCCN)C(=O)NC(CC(C)C)C(=O)NC(Cc3ccc(O)cc3)C(=O)O)C(=O)CN2C1=O]

In some embodiments, the C391 is lipidated.

Indeed, an important aspect of the present invention is that the compositions of the present invention are useful in treating conditions characterized with aberrant PAR$_2$ activity. For example, in some embodiments, compositions comprising PAR$_2$ modulating compounds (e.g., mimetic peptides, small molecules) are used to treat inflammatory conditions through antagonizing PAR$_2$ activity. Such conditions include, but are not limited to, asthma, chronic pain, cancer and/or vascular disorders. In some embodiments, the compositions and methods of the present invention are used to treat cells, tissues, organs, or pathological conditions and/or disease states in an animal (e.g., a mammalian patient including, but not limited to, humans and veterinary animals) having aberrant PAR$_2$ activity. In this regard, various diseases and pathologies are amenable to treatment or prophylaxis using the present methods and compositions. A non-limiting exemplary list of these diseases and conditions includes, but is not limited to, cancers having aberrant activity, inflammatory conditions having aberrant PAR$_2$ activity, asthma, chronic pain, and/or vascular disorders having aberrant PAR$_2$ activity.

Some embodiments of the present invention provide methods for administering an effective amount of a PAR$_2$ modulating compound (e.g., mimetic peptide, small molecule) of the invention and at least one additional therapeutic agent (including, but not limited to, pain relieving agents, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

A number of suitable anti-inflammatory agents are contemplated for use in the methods of the present invention. Examples include steroidal anti-inflammatory agents (e.g., albuterol), and non-steroidal anti-inflammatory agents.

A number of suitable anticancer agents are contemplated for use in the methods of the present invention. Indeed, the present invention contemplates, but is not limited to, administration of numerous anticancer agents such as: agents that induce apoptosis; polynucleotides (e.g., antisense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anti-cancer therapies suitable for co-administration with the disclosed compounds are known to those skilled in the art.

In some embodiments, the pain relieving agents include, but are not limited to, analgesic drugs and respective antagonists. Examples of analgesic drugs include, but are not limited to, paracetamol and Non-steroidal anti-inflammatory drugs (NSAIDs), COX-2 inhibitors, opiates and morphonimimetics, and specific analgesic agents.

Examples of NSAIDs include, but are not limited to, salicylates (e.g., Acetylsalicylic acid (Aspirin), Aloxiprin, Benorylate/Benorilate, Choline magnesium salicylate, Diflunisal, Ethenzamide, Faislamine, Methyl salicylate, Magnesium salicylate, Salicyl salicylate, Salicylamide), arylalkanoic acids (e.g., Diclofenac, Aceclofenac, Acemethacin, Alclofenac, Bromfenac, Etodolac, Indometacin, Nabumetone, Oxametacin, Proglumetacin, Sulindac, Tolmetin), 2-arylpropionic acids (profens) (e.g., Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids (fenamic acids) (e.g., Mefenamic acid, Flufenamic acid, Meclofenamic acid, Tolfenamic acid), pyrazolidine derivatives (e.g., Phenylbutazone, Ampyrone, Azapropazone, Clofezone, Kebuzone, Metamizole, Mofebutazone, Oxyphenbutazone, Phenazone, Sulfinpyrazone), oxicams (e.g., Piroxicam, Droxicam, Lornoxicam, Meloxicam, Tenoxicam), sulphonanilides (e.g., nimesulide), licofelone, and omega-3 fatty acids.

Examples of COX-2 inhibitors include, but are not limited to Celecoxib, Etoricoxib, Lumiracoxib, Parecoxib, Rofecoxib, Valdecoxib.

Examples of opiates include, but are not limited to, natural opiates (e.g., alkaloids contained in the resin of the opium poppy including morphine, codeine and thebaine), semi-synthetic opiates (e.g., created from the natural opioids, such as hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fully synthetic opioids (e.g., such as fentanyl, pethidine, Oxycodone, Oxymorphone, methadone, tramadol, Butorphanol, Levorphanol, and propoxyphene), and endogenous opioid peptides (e.g., produced naturally in the body, such as endorphins, enkephalins, dynorphins, and endomorphins).

Examples of analgesics include, but are not limited to, tricyclic antidepressants (e.g., amitriptyline, carbamazepine, gabapentin, and pregabalin), Tetrahydrocannabinol, ketamine, clonidine, $\alpha_2$-adrenoreceptor agonists, mexiletine, Orphenadrine, cyclobenzaprine, scopolamine, atropine, gabapentin, first-generation antidepressants and other drugs possessing anticholinergic and/or antispasmodic.

In some embodiments, pain-relieving agents include anesthetic drugs. Examples of anesthetic drugs include, but are not limited to, local anesthetics (e.g., procaine, amethocaine, cocaine, lidocaine, prilocaine, bupivacaine, levobupivacaine, ropivacaine, dibucaine), inhaled anesthetics (e.g., Desflurane, Enflurane, Halothane, Isoflurane, Nitrous oxide, Sevoflurane, Xenon), intravenous anesthetics (e.g., Barbiturates (e.g., amobarbital (AMYTAL), pentobarbital (Nembutal), secobarbital (Seconal), Phenobarbital, Methohexital, Thiopental, Methylphenobarbital, Metharbital, Barbexaclone)), Benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze, Triazolam, Etomidate, Ketamine, Propofol).

In some embodiments, pain-relieving agents include anticonvulsant drugs. Examples of anticonvulsant drugs include, but are not limited to, aldehydes (e.g., paraldehyde), aromatic allylic alcohols (e.g., stiripentol), barbiturates (e.g., amobarbital (AMYTAL), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), bromides (e.g., potassium bromide), carbamates (e.g., felbamate), carboxamides (e.g., carbamazepine, oxcarbazepine), fatty acids (e.g., valproates (e.g., valproic acid, sodium valproate, and divalproex sodium), Vigabatrin, Progabide, Tiagabine), fructose derivatives (e.g., topiramate), gaba analogs (e.g., gabapentin, pregabalin), hydantoins (e.g., Ethotoin, Phenytoin, Mephenytoin, Fosphenytoin), Oxazolidinediones (e.g., paramethadione, trimethadione, ethadione), priopionates (e.g., primidone), pyrrolidines (e.g., brivaracetam, levetiracetam, seletracetam), succinimides (e.g., Ethosuximide, Phensuximide, Mesuximide), sulfonamides (e.g., Acetazolamide, Sulthiame, Methazolamide, Zonisamide), triazines (e.g., lamotrigine), ureas (e.g., pheneturide, phenacemide), and valproylamdies (amide derivatives of valproate) (e.g., valpromide, valnoctamide).

In some embodiments, pain-relieving agents include muscle relaxant drugs. Examples of muscle relaxant drugs include, but are not limited to, depolarizing muscle relaxants (e.g., Succinylcholine), short acting non-depolarizing muscle relaxants (e.g., Mivacurium, Rapacuronium), intermediate acting non-depolarizing muscle relaxants (e.g., Atracurium, Cisatracurium, Rocuronium, Vecuronium), and long acting non-depolarizing muscle relaxants (e.g., Alcuronium, Doxacurium, Gallamine, Metocurine, Pancuronium, Pipecuronium, d-Tubocurarine).

In some embodiments, a $PAR_2$ modulating compound (e.g., mimetic peptide, small molecule) of the invention and one or more additional agents (e.g., anti-inflammatory agents, anti-cancer agents, pain-relieving agents) are administered to an animal (e.g., a human patient) under one or more of the following conditions: at different periodicities, at different durations, at different concentrations, by different administration routes, etc. In some embodiments, the $PAR_2$ modulating compound (e.g., mimetic peptide, small molecule) is administered prior to the one or more additional agents (e.g., anti-inflammatory agents, anti-cancer agents, pain-relieving agents), e.g., 0.5, 1, 2, 3, 4, 5, 10, 12, or 18 hours, 1, 2, 3, 4, 5, or 6 days, or 1, 2, 3, or 4 weeks prior to the one or more additional agents (e.g., anti-inflammatory agents, anti-cancer agents, pain-relieving agents). In some embodiments, the $PAR_2$ modulating compound (e.g., mimetic peptide, small molecule) is administered after the one or more additional agents (e.g., anti-inflammatory agents, anti-cancer agents, pain-relieving agents), e.g., 0.5, 1, 2, 3, 4, 5, 10, 12, or 18 hours, 1, 2, 3, 4, 5, or 6 days, or 1, 2, 3, or 4 weeks after the administration of the additional agent. In some embodiments, the $PAR_2$ modulating compound (e.g., mimetic peptide, small molecule) and the additional agent are administered concurrently but on different schedules, e.g., the $PAR_2$ modulating compound (e.g., mimetic peptide, small molecule) is administered daily while the additional agent is administered once a week, once every two weeks, once every three weeks, or once every four weeks. In other embodiments, the $PAR_2$ modulating compound (e.g., mimetic peptide, small molecule) is administered once a week while the additional agent is administered daily, once a week, once every two weeks, once every three weeks, or once every four weeks.

Compositions within the scope of this invention include all compositions wherein the $PAR_2$ modulating compounds (e.g., mimetic peptides, small molecules) of the present invention are contained in an amount that is effective to achieve its intended purpose. While individual needs vary, determination of optimal ranges of effective amounts of each component is within the skill of the art. Typically, the $PAR_2$ modulating compounds (e.g., mimetic peptides, small molecules) may be administered to mammals, e.g. humans, orally at a dose of 0.0025 to 50 mg/kg, or an equivalent amount of the pharmaceutically acceptable salt thereof, per day of the body weight of the mammal being treated for disorders responsive to activation or inhibition of $PAR_2$ activity. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the $PAR_2$ modulating compound (e.g., mimetic peptide, small molecule). The unit dose may be administered one or more times daily as one or more tablets or capsules each containing from about 0.1 to about 10 mg, conveniently about 0.25 to 50 mg of the $PAR_2$ modulating compound (e.g., mimetic peptide, small molecule) or its solvates.

In a topical formulation, the $PAR_2$ modulating compound (e.g., mimetic peptide, small molecule) may be present at a concentration of about 0.01 to 100 mg per gram of carrier. In a one embodiment, the $PAR_2$ modulating compound (e.g., mimetic peptide, small molecule) is present at a concentration of about 0.07-1.0 mg/ml, for example, about 0.1-0.5 mg/ml, and in one embodiment, about 0.4 mg/ml.

In addition to administering the PAR$_2$ modulating compound (e.g., mimetic peptide, small molecule) as a raw chemical, the PAR$_2$ modulating compounds (e.g., mimetic peptides, small molecule) of the invention may be administered as part of a pharmaceutical preparation containing suitable pharmaceutically acceptable carriers comprising excipients and auxiliaries which facilitate processing of the PAR$_2$ modulatign compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active mimetic peptide(s), together with the excipient.

The pharmaceutical compositions of the invention may be administered to any patient that may experience the beneficial effects of the PAR$_2$ modulating compounds (e.g., mimetic peptides, small molecules) of the invention. Foremost among such patients are mammals, e.g., humans, although the invention is not intended to be so limited. Other patients include veterinary animals (cows, sheep, pigs, horses, dogs, cats and the like).

The PAR$_2$ modulating compounds (e.g., mimetic peptides, small molecules) and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active mimetic peptides with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye-stuffs or pigments may be added to the tablets or dragee coatings, for example, for identification or in order to characterize combinations of active mimetic peptide doses.

Other pharmaceutical preparations that can be used orally include push-fit capsules made of gelatin, as well as soft, sealed capsules made of gelatin and a plasticizer such as glycerol or sorbitol. The push-fit capsules can contain the active mimetic peptides in the form of granules that may be mixed with fillers such as lactose, binders such as starches, and/or lubricants such as talc or magnesium stearate and, optionally, stabilizers. In soft capsules, the active mimetic peptides are in one embodiment dissolved or suspended in suitable liquids, such as fatty oils, or liquid paraffin. In addition, stabilizers may be added.

Possible pharmaceutical preparations that can be used rectally include, for example, suppositories, which consist of a combination of one or more of the active mimetic peptides with a suppository base. Suitable suppository bases are, for example, natural or synthetic triglycerides, or paraffin hydrocarbons. In addition, it is also possible to use gelatin rectal capsules that consist of a combination of the active mimetic peptides with a base. Possible base materials include, for example, liquid triglycerides, polyethylene glycols, or paraffin hydrocarbons.

Suitable formulations for parenteral administration include aqueous solutions of the active mimetic peptides in water-soluble form, for example, water-soluble salts and alkaline solutions. In addition, suspensions of the active mimetic peptides as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one that includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention.

Various modifications and alterations of the compositions and methods described above can readily be achieved using expertise available in the art and are within the scope of the invention.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

EXPERIMENTAL

Example I

Protease-activated receptor-2 (PAR$_2$) belongs to a four-member family of G-Protein coupled receptors (GPCRs) that contain internal ligands exposed following exogenous or endogenous protease cleavage of the extracellular amino terminus. PAR$_2$ is associated with a variety of inflammatory conditions, including asthma and pain. The contributions of PAR$_2$ signalling to disease has been hindered by the lack of potent, efficacious antagonists, and their potential for biased-ligand signalling. It was recently demonstrated that lipid tethering of known PAR$_2$ peptidomimetic agonists based on the primary trypsin cleavage sequence (SLIGRL (SEQ ID NO: 19)) increased their potency >200 fold.

Here, lipid tethering (hexadecyl (Hdc) group with polyethylene glycol (PEG) spacers) and heterocycle (2-aminothiazoyl; 2-at) substitution of hexapeptide sequence derived from the primary cleavage site of kallikreins 4/16 (SSKGRS (SEQ ID NO:9)) was used to elucidate novel PAR$_2$ antagonists. Compound 562 (C562), 2-aminothiazol-4yl-SKGRS (SEQ ID NO:10)-PEG$_3$-Hdc blocks PAR$_2$ Ca$^{2+}$ signalling elicited via peptidomimetics (2-at-LIGRL (SEQ ID NO:18)-NH$_2$) or via asthma associated protease activation (*Alternaria alternata* filtrates) in cultured human bronchial epithelial cells (16HBE14o−). This compound was a biased-signalling antagonist in that it had no effect on mitogen activated protein kinase (MAPK) signalling, the other major signalling pathway activated via PAR$_2$. A shortened version of C562, 2-at-SKGR (SEQ ID NO: 6)-PEG$_3$-Hdc (C595), maintained antagonistic activity against peptidomimetic activation in an in vitro physiological signalling assay (xCELLigence). C595 is closely related to the previously described potent and specific PAR$_2$ agonist, 2-at-LIGR (SEQ ID NO: 1)-PEG$_3$-Hdc. Thus, experiments screened a series of potential PAR$_2$ ligands with a heterocycle serine substitute followed by four amino acids (XXGR) and the PEG$_3$-Hdc lipid tether. Several potent agonists are described, and one partial agonist (C608, 2-at-TIGR (SEQ ID NO:4)-PEG$_3$-Hdc) that also acts as a potent, specific and biased signalling antagonist of PAR$_2$. When used in nanomolar concentrations, C608 blocked PAR$_2$-dependent Ca$^{2+}$ signalling via protease or peptidomimetics without effects on MAPK signalling. C562, C595 and C608 are novel pharmacological tools that can be used to evaluate the physiological consequences of PAR$_2$ full and biased ligand signalling.

Figure 2:
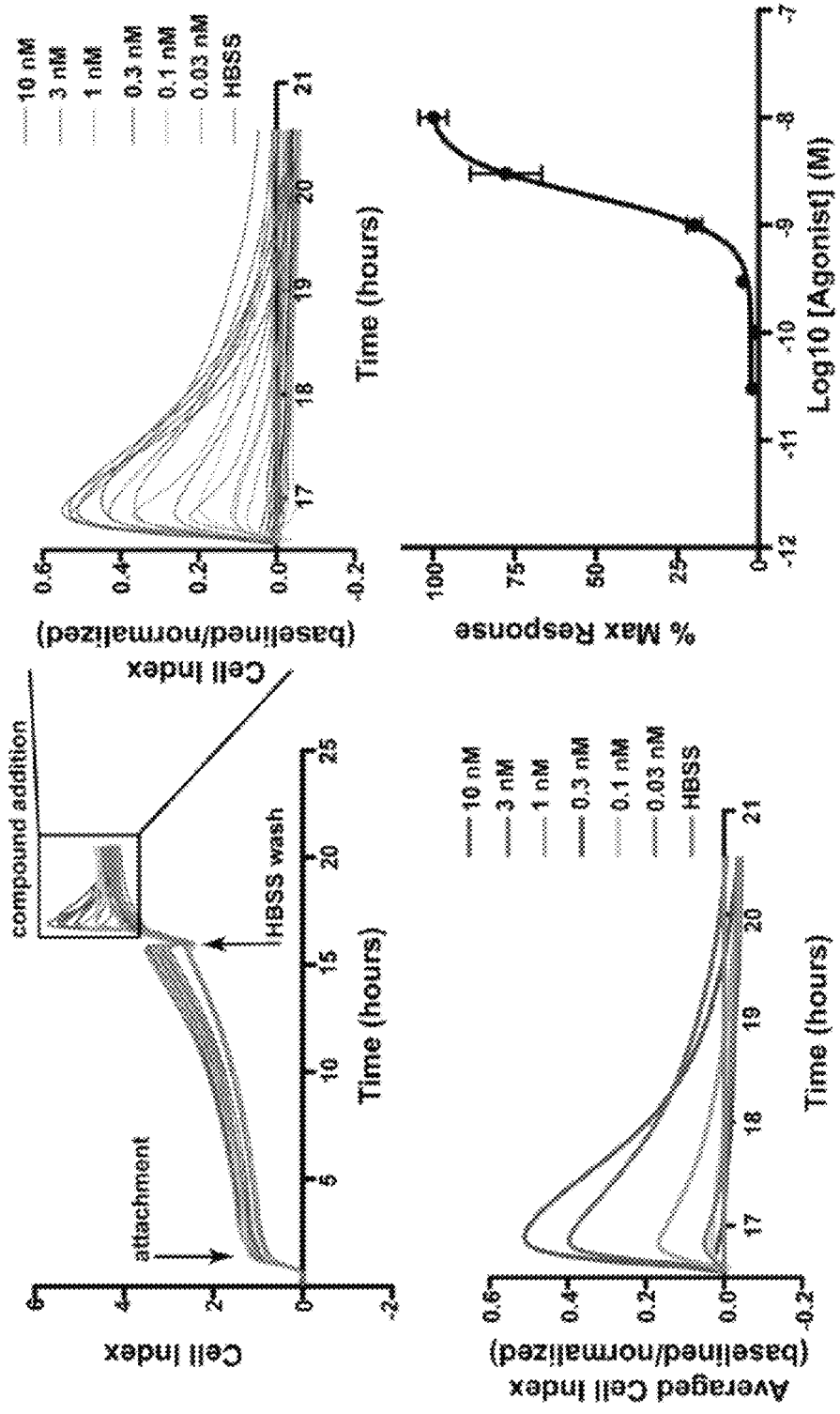
FIG. 2A shows a schematic for PAR$_2$ signalling, and the measuring of PAR$_2$ signalling.
FIG. 2B shows raw traces over time illustrating increases in impedance (Cell Index) over 25 hrs.
FIG. 2C shows transformed traces of agonist addition only, normalized for comparison.
FIG. 2D shows averaged responses from four experiments with appropriate concentration noted at right.
FIG. 2E shows a concentration response curve.

FIG. 2 shows a schematic for PAR$_2$ signalling, and the measuring of PAR$_2$ signalling.

Figure 3:
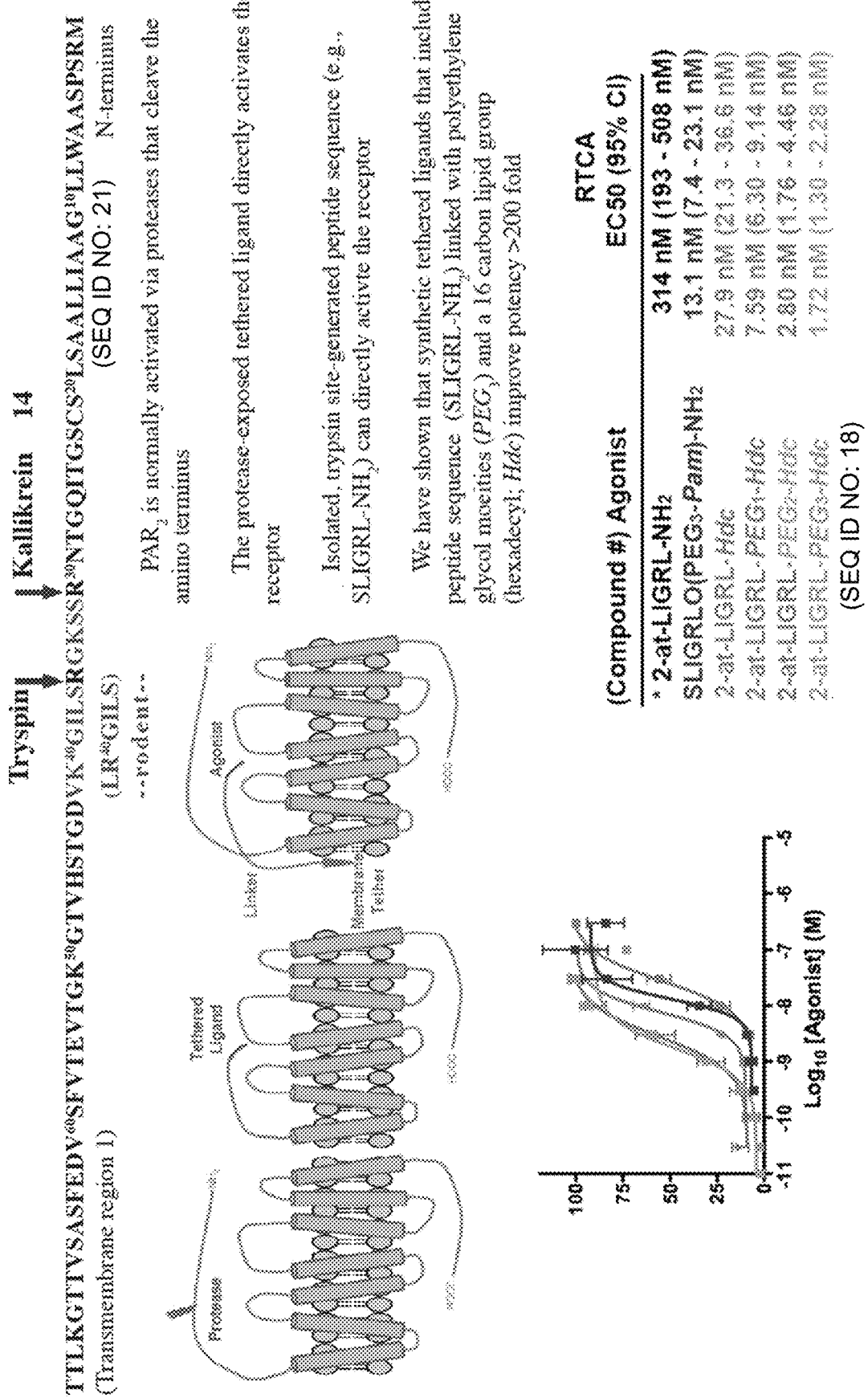
FIG. 3 shows PAR$_2$ tethered ligand probe development—trypsin site.

FIG. 3 shows PAR$_2$ tethered ligand probe development—trypsin site.

Figure 4A:
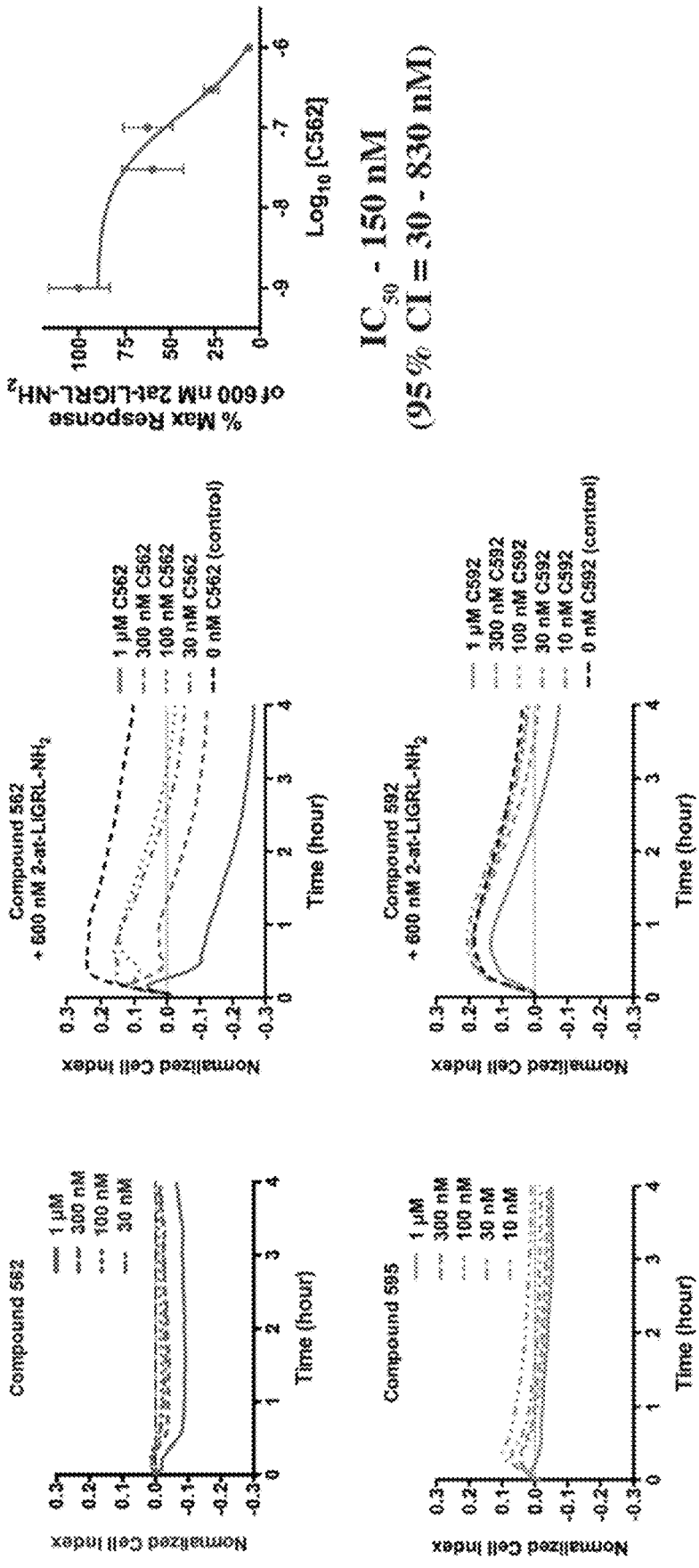
Figure 4C:
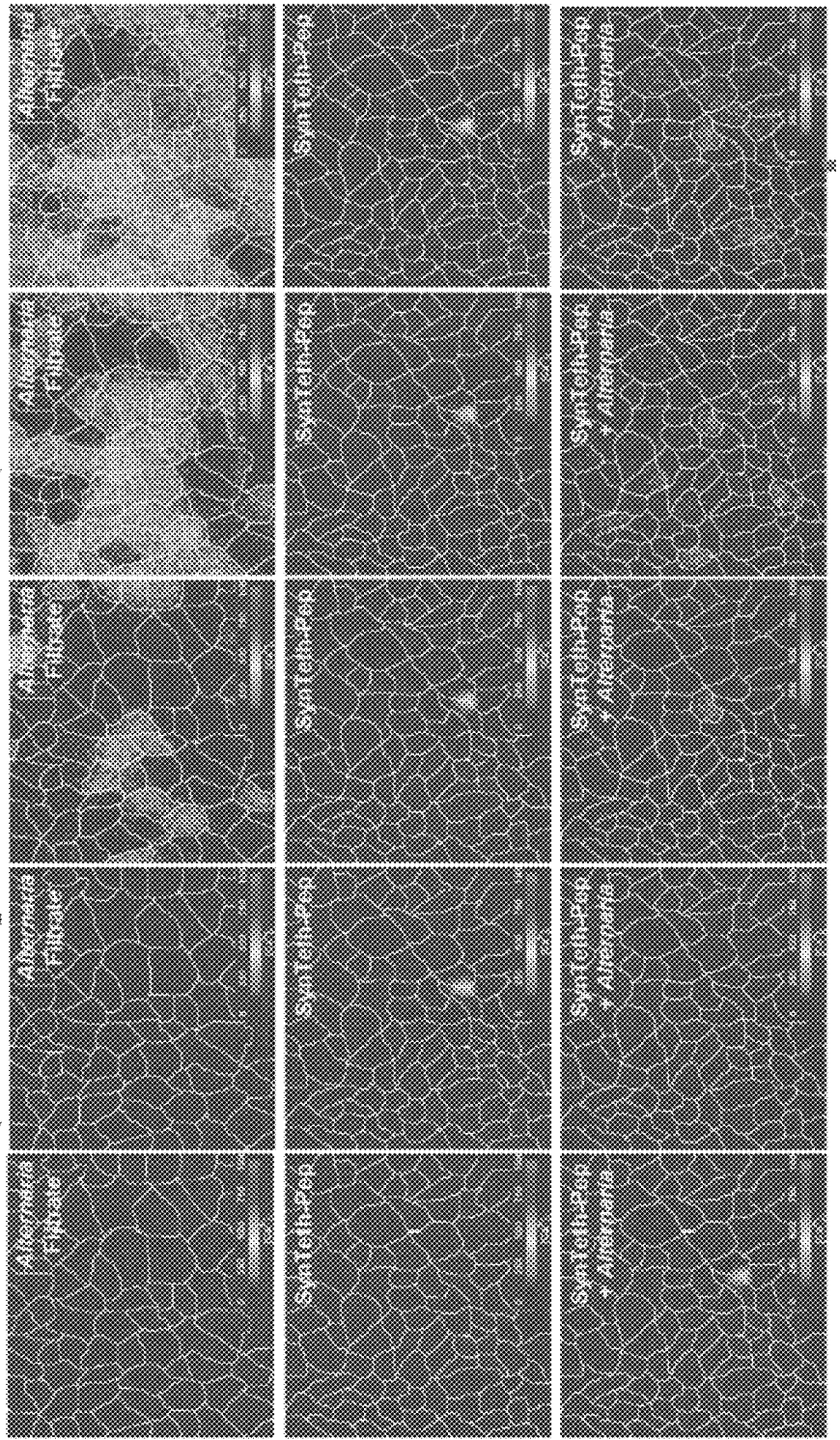

FIG. 4 shows PAR$_2$ tethered ligand probe development—kallikrein site.

Figure 5B:
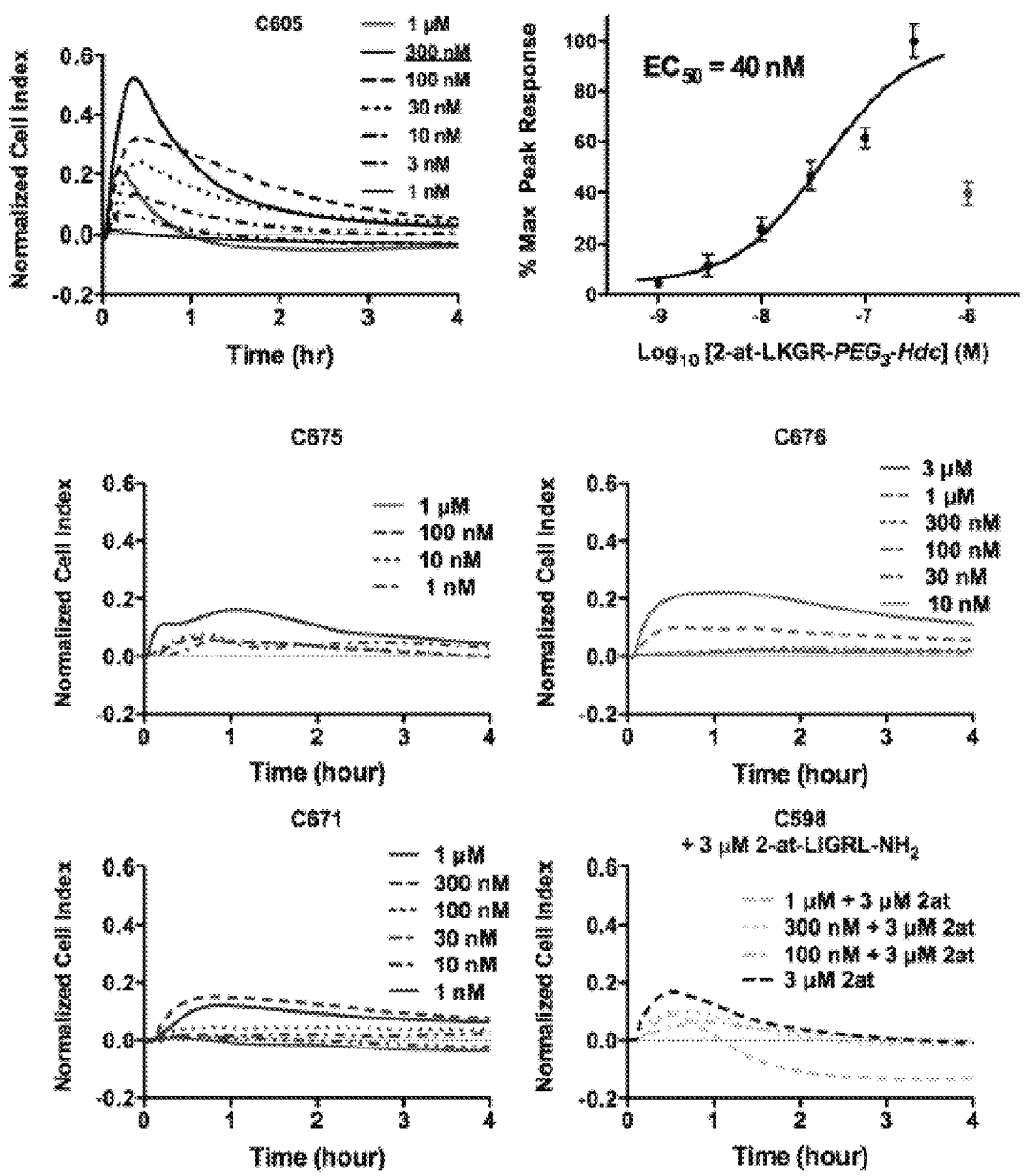

FIG. 5 shows in vitro physiological PAR$_2$ agonist screening using xCELLigence.

Figure 6A:
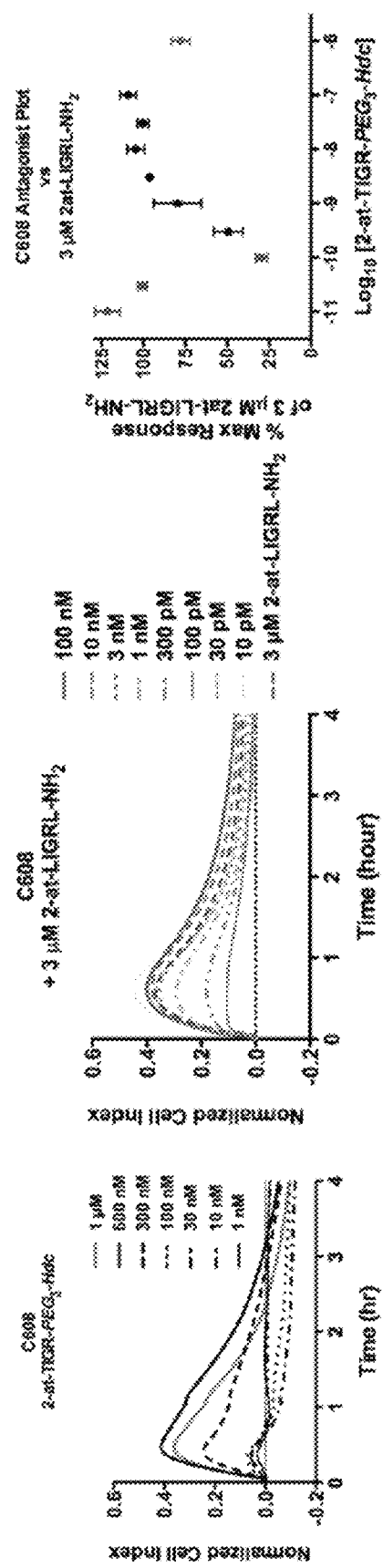
FIGS. 6A-C show 2-at-TIGR (SEQ ID NO:4)-PEG$_3$-Hdc signalling assays.
Figure 6B:
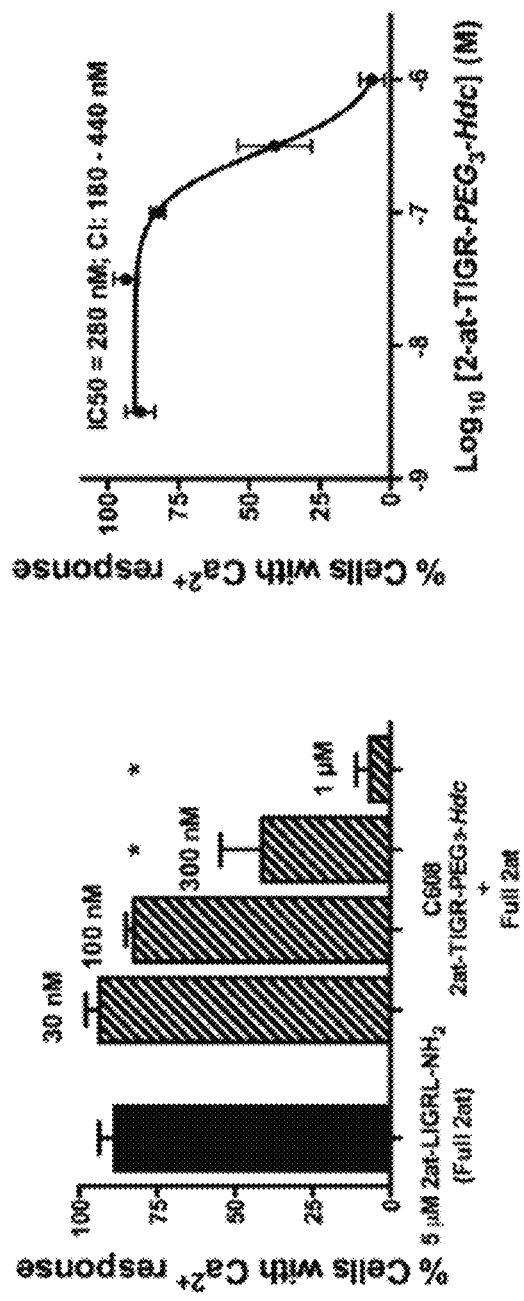
Figure 6C:
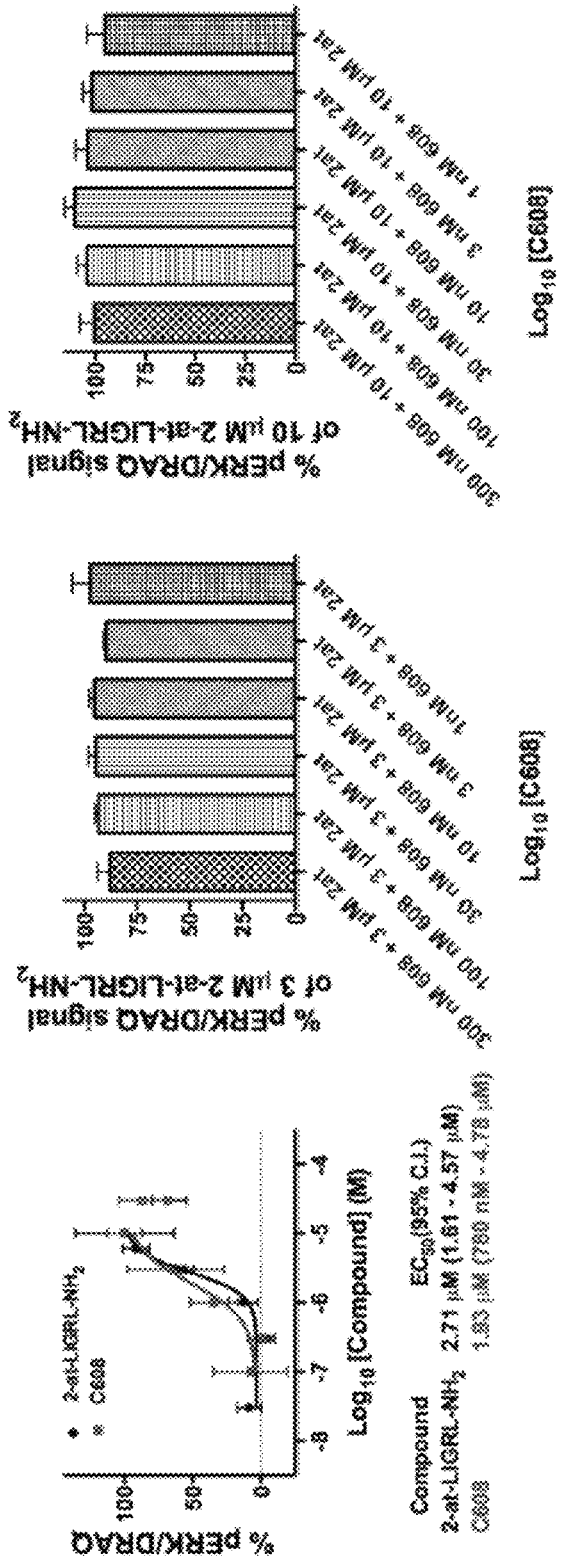

FIG. 6 shows 2-at-TIGR (SEQ ID NO:4)-PEG$_3$-Hdc signalling assays.

Tables 1, 2, 3, 4 and 5 provide additional PAR$_2$ mimetic peptide is configured to modulate PAR$_2$ biological activity.

It was concluded that synthetic tethering allows for screening and development of novel PAR$_2$ ligands.

It was concluded that kallikrein site directed tethered ligands are biased antagonists: a) RTCA signalling antagonists; b) Ca$^{2+}$ signalling anatagonist; c) no effect on MAPK pathways.

It was concluded that C608 is a partial agonist and biased antagonist a) Partial RTCA agonist and potent anatagonist (low concentrations); b) Partial Ca$^{2+}$ signalling agonist and potent antagonist (low concentrations); c) Full MAPK agonist.

It was concluded that a partial and biased agonist/antagonist can provide novel in vivo applications.

TABLE 1

Kallikrein Peptide Sequence with Truncations

| Compound # in Order of appearance | Compound Name | Compound Summary as Determined by RTCA Screen |
|---|---|---|
| 1 | SSKGRSO-NH2 | Not Included |
| 2 | 2at-SKGRSO-NH2 | Not Included |
| 3 | SSKGRSO-PEG$_3$-Pam | Not Included |
| 4 | 2at-SKGRSO-PEG$_3$-Pam | Not Included |
| 5 | 2at-SKGRS-PEG$_3$-Hdc | PAR2 Antagonist |
| 6 | 2at-SKGR-PEG$_3$-Hdc | Reduces a PAR2 physiological response |

TABLE 2 amino acid substitutions based on truncated of 2at-SKGR-PEG$_3$-Hdc from above to try to improve truncation

| Compound # in Order of appearance | Compound Name | Compound Summary as Determined by RTCA Screen |
|---|---|---|
| 7 | 2at-SRGR-PEG$_3$-Hdc | No Activity at PAR2 Detected |
| 8 | 2at-SHGR-PEG$_3$-Hdc | No Activity at PAR2 Detected |
| 9 | 2at-S-Dap-GR-PEG$_3$-Hdc | Reduces a PAR2 physiological response |
| 10 | 2at-TKGR-PEG$_3$-Hdc | No Activity at PAR2 Detected |
| 11 | 2at-LKGR-PEG$_3$-Hdc | Full PAR2 Agonist |

TABLE 3 amino acid L2 substitutions of 2at-LIGR-PEG$_3$-Hdc to assess block based 2at-X-IGR (Note premise thought better binding from this sequence)

| Compound # in Order of appearance | Compound Name | Compound Summary as Determined by RTCA Screen |
|---|---|---|
| 12 | 2at-LIGR-PEG$_3$-Hdc | Full PAR2 Agonist |
| 13 | 2at-SIGR-PEG$_3$-Hdc | No Activity at PAR2 Detected |
| 14 | 2at-TIGR-PEG$_3$-Hdc | PAR2 Agonist and Antagonist |
| 15 | 2at-DIGR-PEG$_3$-Hdc | No Activity at PAR2 Detected |
| 16 | 2at-HIGR-PEG$_3$-Hdc | PAR2 Agonist |
| 17 | 2at-VIGR-PEG$_3$-Hdc | PAR2 Agonist |

TABLE 4 non-lipidated TIGR

| Compound # in Order of appearance | Compound Name | Compound Summary as Determined by RTCA Screen |
|---|---|---|
| 18 | 2at-TIGR-NH2 | No Classical Activation or Block at PAR2 |
| 19 | 2at-TIGRL-NH2 | No Classical Activation or Block at PAR2 |

TABLE 5 alternative amino acid L2 substitutions of 2at-LIGRL-PEG$_3$-Hdc

| Compound # in Order of appearance | Compound Name | Compound Summary as Determined by RTCA Screen |
|---|---|---|
| 20 | 2at-hydroxyproline-IGR-PEG$_3$-Hdc | No Activity at PAR2 Detected |
| 21 | 2at-homoserine-IGR-PEG$_3$-Hdc | PAR2 Agonist |
| 22 | 2at-penicillamine-IGR-PEG$_3$-Hdc | No Activity at PAR2 Detected |
| 23 | 2at-4thiazolamine-IGR-PEG$_3$-Hdc | No Activity at PAR2 Detected |
| 24 | 2at-(dL)IGR-PEG$_3$-Hdc | No Activity at PAR2 Detected |
| 25 | 2at-(dl)IGR-PEG$_3$-Hdc | No Activity at PAR2 Detected |
| 26 | 2at-(dT)IGR-PEG$_3$-Hdc | No Activity at PAR2 Detected |

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes.

What is claimed is:

1. A composition comprising a protease activator receptor type-2 (PAR2) mimetic peptide having Formula I:
[heterocycle moiety]-[peptide sequence]-[linker moiety]-[cell membrane anchoring moiety], including pharmaceutically acceptable salts, lipidated analogs, pegylated analogs, and/or prodrugs thereof;
wherein the heterocycle is selected from the group consisting of an aminothiazoyl moiety, a penicillamine moiety, a homoserine moiety, a thiazolamine moiety, and a hydroxyproline moiety;
wherein the linker moiety is one or more polyethylene glycol (PEG) moieties;
wherein the cell membrane anchoring moiety is hexadecyl;
wherein the PAR2 mimetic peptide is configured to activate or inhibit PAR2 biological activity, and
wherein the peptide sequence is the amino acid sequence selected from the group consisting of Ile-Gly,
Ile-Gly-Arg,
Ser-Leu-Ile-Gly (SEQ ID NO:2),
Thr-Ile-Gly,
Thr-Ile-Gly-Arg (SEQ ID NO:4),
Ser-Lys-Gly-Arg-Ser (SEQ ID NO:5),
Ser-Lys-Gly-Arg (SEQ ID NO:6),
His-Ile-Gly-Arg (SEQ ID NO:7),
Val-Ile-Gly-Arg (SEQ ID NO:8),
Ser-Lys-Gly-Ser (SEQ ID NO: 22),
Gly-Arg-Ser,
Ser-Lys-Arg-Ser (SEQ ID NO: 23), and
Leu-Lys-Gly-Arg (SEQ ID NO: 14).

2. The composition of claim 1, wherein the $PAR_2$ mimetic peptide is selected from [2-aminothiazoyl]-[His-Ile-Gly-Arg (SEQ ID NO: 7)]-[$PEG_3$]-[hexadecyl], [2-aminothiazoyl]-[Val-Ile-Gly-Arg (SEQ ID NO: 8)]-[$PEG_3$]-[hexadecyl], [2-aminothiazoyl]-[(homoserine)IGR]-[$PEG_3$]-[hexadecyl], [2-aminothiazoyl]-[Thr-Ile-Gly-Arg (SEQ ID NO:4)]-[$PEG_3$]-[hexadecyl], [2-aminothiazoyl]-[Ser-Lys-Gly-Arg-Ser (SEQ ID NO:5)]-[$PEG_3$]-[hexadecyl], and [2-aminothiazoyl]-[Ser-Lys-Gly-Arg (SEQ ID NO:6)]-[$PEG_3$]-[hexadecyl].

3. A method for activating or inhibiting the activity of $PAR_2$ in a subject, comprising administering to the subject in need thereof a composition as recited in claim 1.

4. The method of claim 3, wherein the subject has or is experiencing aberrant $PAR_2$ activity.

5. The method of claim 3, wherein the subject is a human subject.

6. The method of claim 3, wherein the subject has or is at risk for developing an inflammatory condition involving aberrant $PAR_2$ activity.

* * * * *

UNITED STATES PATENT AND TRADEMARK OFFICE
CERTIFICATE OF CORRECTION

| | | |
|---|---|---|
| PATENT NO. | : 11,351,264 B2 | |
| APPLICATION NO. | : 16/090525 | |
| DATED | : June 7, 2022 | |
| INVENTOR(S) | : Scott Boitano, Josef Vagner and Theodore Price | |

It is certified that error appears in the above-identified patent and that said Letters Patent is hereby corrected as shown below:

In the Claims

Column 33, Claim 1, Line 37 reads:
wherein the heterocycle is
Whereas it should read:
wherein the heterocycle moiety is Signed and Sealed this
Eleventh Day of October, 2022

Katherine Kelly Vidal
*Director of the United States Patent and Trademark Office*